US009642709B2

(12) United States Patent
Boedo et al.

(10) Patent No.: US 9,642,709 B2
(45) Date of Patent: May 9, 2017

(54) ARTIFICIAL HIP JOINT REPLACEMENT SYSTEM

(71) Applicants: CORNELL UNIVERSITY, Ithaca, NY (US); ROCHESTER INSTITUTE OF TECHNOLOGY, Rochester, NY (US)

(72) Inventors: Stephen Boedo, Canandaigua, NY (US); John F. Booker, Ithaca, NY (US)

(73) Assignees: Cornell University, Ithaca, NY (US); Rochester Institute of Technology, Rochester, NY (US)

( * ) Notice: Subject to any disclaimer, the term of this patent is extended or adjusted under 35 U.S.C. 154(b) by 0 days.

(21) Appl. No.: 14/427,218

(22) PCT Filed: Sep. 11, 2013

(86) PCT No.: PCT/US2013/059266
§ 371 (c)(1),
(2) Date: Mar. 10, 2015

(87) PCT Pub. No.: WO2014/043236
PCT Pub. Date: Mar. 20, 2014

(65) Prior Publication Data
US 2015/0342740 A1     Dec. 3, 2015

Related U.S. Application Data

(60) Provisional application No. 61/699,438, filed on Sep. 11, 2012.

(51) Int. Cl.
*A61F 2/32*     (2006.01)
*A61F 2/34*     (2006.01)
(Continued)

(52) U.S. Cl.
CPC ............... *A61F 2/34* (2013.01); *A61F 2/32* (2013.01); *A61F 2/36* (2013.01); *A61F 2/3609* (2013.01);
(Continued)

(58) Field of Classification Search
CPC ...... A61F 2/32; A61F 2/34; A61F 2/36; A61F 2002/30563; A61F 2002/30565;
(Continued)

(56) References Cited

U.S. PATENT DOCUMENTS 4,044,403 A     8/1977 D'Errico
4,408,360 A     10/1983 Keller
(Continued)

OTHER PUBLICATIONS

PCT International Search Report and Written Opinion for corresponding international application PCT/US2013/059266 (mailed Jan. 16, 2014).

*Primary Examiner* — David Isabella
*Assistant Examiner* — Dinah Baria
(74) *Attorney, Agent, or Firm* — LeClairRyan, a Professional Corporation

(57) ABSTRACT

The present invention relates to an artificial hip joint replacement system. The system includes an acetabulum portion having a cup suitable to be received by a subject's acetabular bone. The cup includes a rigid portion and an elastic portion attached to the rigid portion. Also included in the system is a ball received within the cup and in contact with the elastic portion and a femoral stem attached to the ball. The elastic portion is positioned to cause expansion and allow contraction of a space between the ball and the rigid portion of the cup so they are further apart from one another during periods of low mechanical loads.

22 Claims, 23 Drawing Sheets

(51) Int. Cl.
*A61F 2/36* (2006.01)
*A61F 2/30* (2006.01)

(52) U.S. Cl.
CPC ............... *A61F 2002/30253* (2013.01); *A61F 2002/30563* (2013.01); *A61F 2002/30565* (2013.01); *A61F 2002/30571* (2013.01); *A61F 2002/30594* (2013.01); *A61F 2002/30673* (2013.01); *A61F 2002/30934* (2013.01); *A61F 2002/30937* (2013.01); *A61F 2002/3225* (2013.01); *A61F 2002/3611* (2013.01); *A61F 2002/3617* (2013.01); *A61F 2002/3623* (2013.01); *A61F 2230/0093* (2013.01); *A61F 2230/0095* (2013.01)

(58) Field of Classification Search
CPC .. A61F 2002/30576; A61F 2002/30937; A61F 2002/3617; A61F 2002/30253; A61F 2002/3024; A61F 2002/30245; A61F 2002/30247; A61F 2002/3025; A61F 2002/3409; A61F 2002/3412; A61F 2002/3417
See application file for complete search history.

(56) References Cited

U.S. PATENT DOCUMENTS

| | | | | |
|---|---|---|---|---|
| 4,718,911 | A | | 1/1988 | Kenna |
| 5,019,105 | A | * | 5/1991 | Wiley ....................... A61F 2/34 623/22.29 |
| 5,593,445 | A | * | 1/1997 | Waits .................... A61F 2/3099 623/23.39 |
| 5,645,606 | A | * | 7/1997 | Oehy .................. A61F 2/30744 623/22.34 |
| 7,914,580 | B2 | * | 3/2011 | Kellar ................. A61F 2/30767 623/16.11 |
| 2005/0085915 | A1 | | 4/2005 | Steinberg |
| 2012/0221115 | A1 | * | 8/2012 | Komistek ................. A61F 2/32 623/22.15 |
| 2013/0304225 | A1 | * | 11/2013 | Komistek ................. A61F 2/34 623/22.16 |

\* cited by examiner

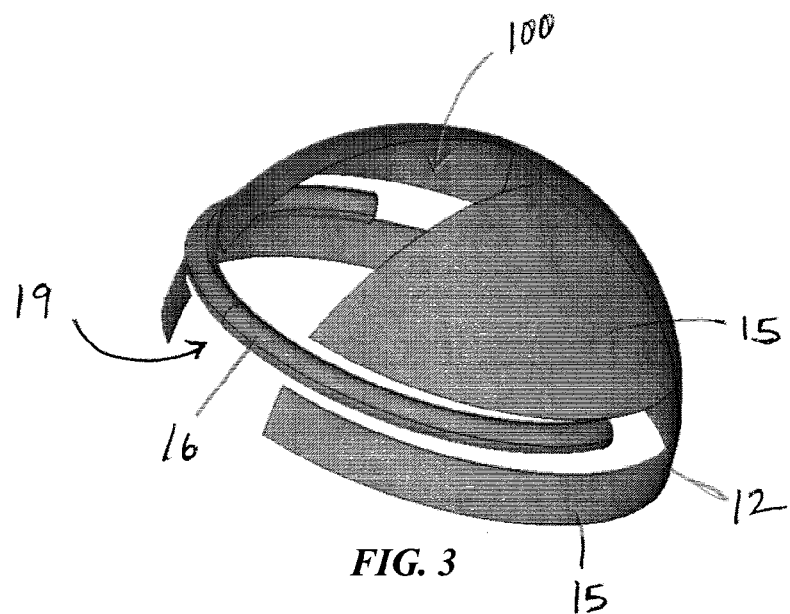
*FIG. 3*
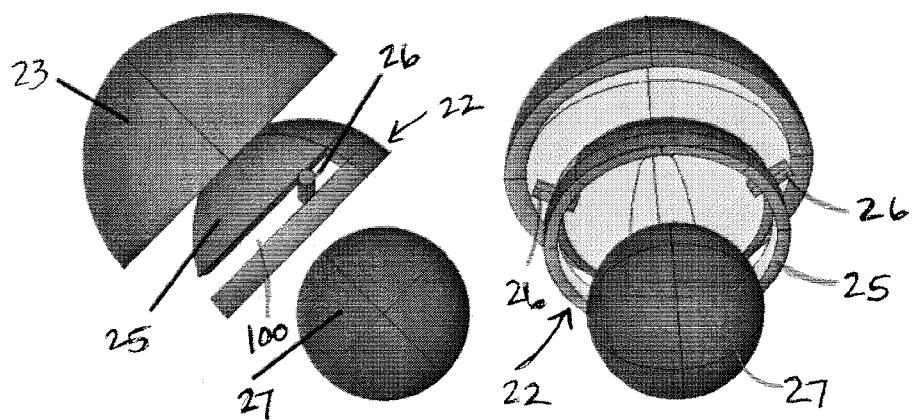
*FIG. 4A*  *FIG. 4B*

ARTIFICIAL HIP JOINT REPLACEMENT SYSTEM

This application is a national stage application under 35 U.S.C. 371 from PCT Application No. PCT/US2013/059266, filed Sep. 11, 2013, which claims the benefit of U.S. Provisional Patent Application Ser. No. 61/699,438, filed Sep. 11, 2012, which are hereby incorporated by reference in their entirety.

FIELD OF THE INVENTION

The present invention relates to an artificial hip joint replacement system.

BACKGROUND OF THE INVENTION

Total hip arthroplasty refers to the replacement of natural hip joint components with artificial ball and socket devices of various complexity and configurations. A generally spherical ball comprised of metallic or ceramic materials is often attached to an artificial femoral stem implanted in the femur, while a generally hemispherical socket is implanted into a surgically modified acetabulum.

Artificial hip joint designs are typically classified according to the paired materials employed in the prosthesis. In "metal-on-metal" designs, both ball and socket are comprised of various metallic alloys (such as stainless steel, CoCr, and CoCrMo), as exemplified in U.S. Pat. No. 3,848,272 to Noiles and U.S. Pat. No. 7,361,194 to Carroll. In "ceramic-on-metal" or "ceramic-on-ceramic" designs, a ceramic ball (typically comprised of alumina or zirconia) is attached to a metallic or ceramic femoral stem while the socket is comprised of ceramic materials or various metallic alloys (such as stainless steel, CoCr, or CoCrMo), as exemplified in U.S. Pat. No. 6,881,229 to Khandkar et al.; U.S. Pat. No. 5,788,916 to Caldarise; and U.S. Pat. No. 3,924,275 to Heimke et al. In "metal-on-plastic" or "ceramic-on-plastic" designs, the ball is comprised of either metallic or ceramic materials while the socket is comprised of a plastic hemispherical cup (typically comprised of ultra-high-molecular-weight polyethylene (UHMWPE)) which is attached in various ways to a metallic shell, as exemplified in U.S. Pat. No. 5,080,677 to Shelley.

A continuing problem with current artificial hip joint replacements is wear of the articulating surfaces. In metal-on-plastic designs, wear particles from the relatively softer UHMWPE material can generate an autoimmune reaction in the body known as osteolysis which results in resorption of living bone tissue surrounding the artificial socket and subsequent loosening or detachment of the socket from the acetabulum. In metal-on-metal designs, high concentrations of metallic ions associated with nanoscale wear particles have been found deposited in the surrounding tissue, and these high ion concentrations may pose long-term health concerns.

Aggravated wear is linked to the lack of full-film lubrication prevalent with current artificial hip joint designs. Synovial fluid is generated in body tissues surrounding the artificial hip joint. The load transmitted from ball to cup varies in magnitude and direction but does not reverse direction during the gait cycle. Thus, the only mechanism then capable of supplying synovial fluid to the joint is "wedge-film" action generated by relative tangential surface motions associated with the gait cycle kinematics. Even though ball and cup contacting surfaces are conformal, the ball and cup elastic properties, load magnitude, and the surfaces' radii of curvature result in a load-carrying lubricated contact region which covers only a small percentage of the total possible surface contact area. Elastohydrodynamic analysis methods appropriate for such locally lubricated contacts predict minimum film thickness values on the order of 40 to 60 nm (Mattei et al., "Lubrication and Wear Modelling of Artificial Hip Joints: A Review," *Tribology International* 44:532-549 (2011)) which when compared with surface roughness values are generally in the boundary to mixed-lubrication regime. Contacting surfaces operating in these regimes of lubrication are not completely separated, resulting in surface wear generated by either direct contact of surface asperities (adhesion wear) or through wear particles wedged between the surfaces (abrasive wear). Compounding the lubrication and wear problem is the observance of relatively thick protein layers which are in suspension in the synovial fluid and which are accumulated on the articulating surfaces in the contact region. These protein layers can be on the order of 100 nm thick (Sprecher et al., "Solid Lubrication—A Relevant Lubrication Mechanism for Reducing Wear in Metal-on-Metal THA Components?" In 49th Annual Meeting, ORS, p. 1391 (2003)).

Manufacturing and fabrication concerns are also prevalent with current artificial hip joint designs. Ceramic-on-ceramic designs are prone to squeaking during walking, presumably due to stick-slip friction developed between the articulating surfaces (Feder "That Must Be Bob. I Hear his New Hip Squeaking," The New York Times, May 11, 2008 (2008)). Ceramic-on-ceramic designs are also relatively more expensive and brittle in nature, so particular attention is needed for both fabrication and surgical procedure.

In U.S. Pat. No. 5,609,646 to Field et al., an artificial acetabular component is comprised of an outer reinforcing backing and an inner bearing component, the latter of which has two independent protruding arms. The intent of this arrangement is to provide adequate flexibility and accommodate deformation of the natural portion of the acetabulum under loading. In U.S. Patent Application Publication No. 2009/0259317 to Steinberg, an elastic socket insert is described. U.S. Pat. No. 6,248,132 to Harris describes an interior spring assembly placed between the outer shell and inner cup which acts as a shock absorber during the load phase of the gait cycle. In U.S. Pat. No. 5,788,916 to Caldarise, a set of leaf springs are formed in the outer metallic shell which also acts as a shock absorber during the load phase of the gait cycle. In U.S. Patent Application Publication No. 2001/0051831 to Rao et al. and U.S. Pat. No. 5,389,107 to Nassar et al., an interior spring and shock absorbing materials are connected between the ball and femoral stem. These patents and patent applications all assume that the ball and cup surfaces will come into contact with each other, and the structural elasticity described in these patents is employed to mitigate impact damage and dampen stress waves induced from contact. None of these documents pertain to squeeze-film fluid action to keep the load-carrying surfaces apart, nor do they provide an elastic spring contact connection between ball and cup to intentionally separate the surfaces during the (unloaded) swing phase of the gait cycle.

In U.S. Pat. No. 5,879,386 to Jore, natural magnetic materials inserted into the bone provide repelling forces between articulating joints. U.S. Patent Application Publication No. 2002/0087213 to Bertram employs magnetic materials to provide repelling forces between the ball and cup in order to stabilize hip joint motion. Neither of these documents provides a mechanical means to separate the surfaces in the manner described in the present invention.

In GB Patent No. 1,192,555 to New, a set of two struts provide a connection between the wristpin and connecting rod in a cylindrical bearing arrangement appropriate for two-stroke engines where the external piston load is variable in magnitude but does not reverse direction. These struts provide a mechanical means of separating the wristpin bearing surface from the small-end sleeve surface when the external load magnitude is minimal over the engine cycle. However, the particular design of the strut geometry and the interaction of the strut with hemispherical contact surfaces built into the wristpin restrict this embodiment to cylindrical journal bearing geometry where journal translation (relative to sleeve) and external loads are planar (two-dimensional) and where the rotation of the sleeve relative to the journal is about a single axis normal to the plane. In addition, GB Patent No. 1,192,555 to New places the positioning of the mechanical spring mechanism external to the bearing region.

In Meng et al., "Contact Mechanics and Elastohydrodynamic Lubrication in a Novel Metal-on-Metal Hip Implant with an Aspherical Bearing Surface," *Journal of Biomechanics* 43:849-857 (2012); European Patent No. 0748193 to Fisher; and PCT Publication No. WO/1995/023566 to Fisher, non-spherical ball and cup articulating surfaces are described. However, none of these documents pertain to squeeze-film fluid action to keep the load-carrying surfaces apart nor do these documents provide an elastic contact connection between ball and cup to intentionally separate the surfaces during the (unloaded) swing phase of the gait cycle.

The present invention is directed to overcoming deficiencies in the art.

SUMMARY OF THE INVENTION

One aspect of the present invention relates to an artificial hip joint replacement system. This system includes an acetabulum portion comprising a cup suitable to be received by a subject's acetabular bone. The cup includes a rigid portion and an elastic portion attached to the rigid portion. Also included in the system is a ball received within the cup and in contact with the elastic portion and a femoral stem attached to the ball. The elastic portion is positioned to cause expansion and contraction of a space between the ball and the rigid portion of the cup so they are further apart from one another during periods of low mechanical loads.

Another aspect of the present invention relates to an artificial hip joint replacement system. This system includes an acetabular portion comprising a cup suitable to be received by a subject's acetabular bone. The cup includes a rigid portion and an elastic portion attached to the rigid portion. Also included in the system is a ball received within the cup and in contact with the elastic portion and a femoral stem attached to the ball. The elastic portion is positioned to allow expansion and contraction of a space between the ball and the rigid portion of the cup so that the ball and the rigid portion of the cup move apart from one another during periods of low mechanical loads.

A further aspect of the present invention also relates to an artificial hip joint replacement system. This system includes an acetabular portion comprising a cup suitable to be received by a subject's acetabular bone. The system also includes a ball comprising a rigid portion and an elastic portion attached to the rigid portion. The ball is received within the cup with the elastic portion of the ball being in contact with the cup. Also included in the system is a femoral stem attached to the ball. The elastic portion of the ball is positioned to allow expansion and contraction of a space between the ball and the cup so that the ball and the cup move apart from one another during periods of low mechanical loads.

Yet another aspect of the present invention also relates to an artificial hip joint replacement system. This system includes an acetabular portion comprising a cup suitable to be received by a subject's acetabular bone. The system also includes a ball received within the cup and an elastic element in contact with the ball and the cup. The elastic element is positioned to allow expansion and contraction of a space between the ball and the cup so that the ball and the cup move apart from one another during periods of low mechanical loads. The system also includes a femoral stem attached to the ball.

In the artificial hip joint replacement system of the present invention, an elastic portion provides mechanical spring action, which takes into account ball translation, ball rotation, and external ball loading about three mutually perpendicular axes. According to the present invention, an artificial hip joint replacement system is configured so that it makes significant improvements in bearing performance over conventional designs. Elastic elements and an aspherical cup surface (and/or aspherical ball) are incorporated into the system to promote and enhance squeeze-film action of joint synovial fluid, thereby alleviating sole reliance on wedge-film action and encouraging larger film thickness and smaller film pressures.

BRIEF DESCRIPTION OF THE DRAWINGS

FIG. 3 is an exploded, perspective view of one embodiment of a cup of the acetabular portion of the artificial hip joint replacement system of the present invention. According to this embodiment, the elastic portion of the cup comprises a curved beam of circular cross-section in its unstressed state, which protrudes into the ball-cup clearance space to contact a ball received within the cup.

FIGS. 4A-C illustrate component parts of one embodiment of an artificial hip joint replacement system of the present invention. FIG. 4A is an anterior exploded view of a shell, a cup, and a ball. FIG. 4B is a lateral exploded view of a shell, a cup, and a ball. FIG. 4C is a perspective view of a cup suitable to be received by a subject's acetabular bone, where the cup includes a rigid portion and elastic portions attached to the rigid portion which protrude into the ball-cup clearance space to contact a ball received within the cup.

FIG. 5A is a perspective view of this embodiment. FIG. 5B is a cross-sectional frontal view of this embodiment.

FIG. 6A is a perspective view of the rigid portion showing various axes. FIG. 6B is an exaggerated plan view showing aspherical angles.

FIG. 10A is a cross-sectional, side view of the system implanted into a human acetabular bone. FIG. 10B is a perspective review of the ball component and elastic element component of the system. FIG. 10C is an exploded view of the ball component and elastic element component of the system.

FIG. 17A refers to a cup geometry with ellipticity parameter $\delta$=30 µm defined below. FIG. 17B refers to a cup geometry with ellipticity parameter $\delta$=40 µm defined below. FIG. 17C refers to a cup geometry with ellipticity parameter $\delta$=50 µm defined below.

In FIG. 18A, each curve gives the minimum film thickness encountered over the stance phase of the gait cycle as a function of specified cup ellipticity parameter $\delta$. In FIG. 18B, each curve gives the maximum film pressure encountered over the stance phase of the gait cycle as a function of specified cup ellipticity parameter $\delta$.

In FIG. 19A, each curve gives the minimum film thickness encountered over the stance phase of the gait cycle as a function of specified cup ellipticity parameter $\delta$. In FIG. 19B, each curve gives the maximum film pressure encountered over the stance phase of the gait cycle as a function of specified cup ellipticity parameter $\delta$.

FIG. 22A compares the time history of minimum film thickness during the stance phase of the gait cycle. FIG. 22B compares the time history of ball motion during the stance phase of the gait cycle.

In FIG. 23A, each curve gives the minimum film thickness encountered over the stance phase of the gait cycle as a function of specified cup ellipticity parameter $\delta$. In FIG. 23B, each curve gives the maximum film pressure encountered over the stance phase of the gait cycle as a function of specified cup ellipticity parameter $\delta$.

In FIG. 24A, each curve gives the periodic time history of minimum film thickness encountered over the entire periodic gait cycle. In FIG. 24B, each curve gives the periodic time history of maximum film pressure encountered over the entire periodic gait cycle.

FIG. 28A shows a sectional view of the rigid portion of the cup. FIG. 28B shows a sectional view of the rigid and elastic portions of the cup, the latter of which is represented by columns of circular cross-section.

DETAILED DESCRIPTION OF THE INVENTION

The present invention relates to an artificial hip joint replacement system. According to one aspect, the present invention relates to an artificial hip joint replacement system. This system includes an acetabulum portion comprising a cup suitable to be received by a subject's acetabular bone. The cup includes a rigid portion and an elastic portion attached to the rigid portion. Also included in the system is a ball received within the cup and in contact with the elastic portion and a femoral stem attached to the ball. The elastic portion is positioned to cause expansion and contraction of a space between the ball and the rigid portion of the cup so they are further apart from one another during periods of low mechanical loads.

According to another aspect, the present invention relates to an artificial hip joint replacement system. This system includes an acetabular portion comprising a cup suitable to be received by a subject's acetabular bone. The cup includes a rigid portion and an elastic portion attached to the rigid portion. Also included in the system is a ball received within the cup and in contact with the elastic portion and a femoral stem attached to the ball. The elastic portion is positioned to allow expansion and contraction of a space between the ball and the rigid portion of the cup so that the ball and the rigid portion of the cup move apart from one another during periods of low mechanical loads.

In the following description, reference is made to the accompanying drawings that form a part hereof, and in which is shown by way of illustration specific embodiments which may be practiced. These embodiments are described in sufficient detail to enable those skilled in the art to practice the invention, and it is to be understood that other embodiments may be utilized and that structural, logical, mechanical, and other changes may be made without departing from the scope of the present invention. The following description of exemplary embodiments is, therefore, not to be taken in a limited sense.

Figure 1:
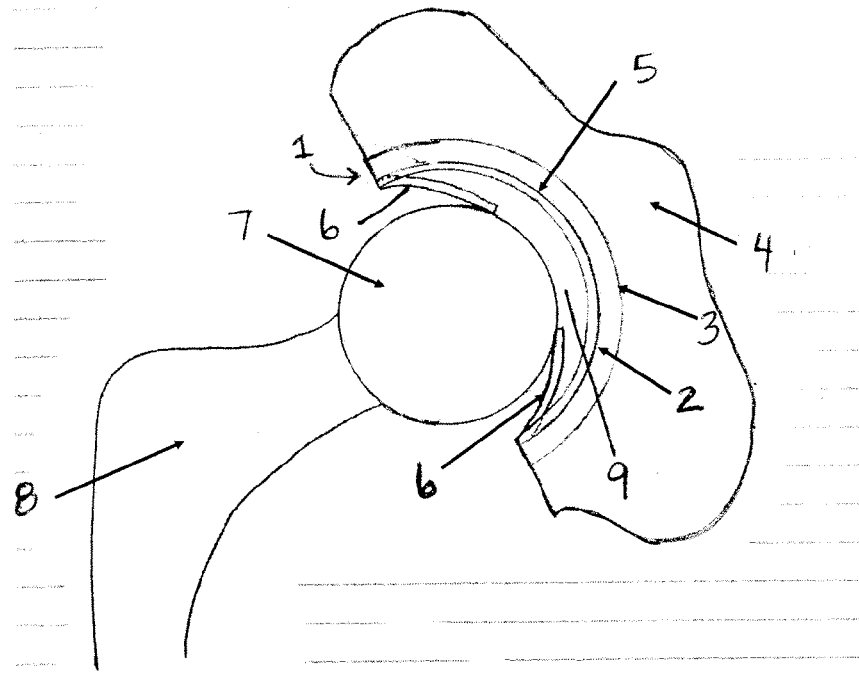
FIG. 1 is a cross-sectional, side view of one embodiment of an artificial hip joint replacement system of the present invention implanted into a human acetabular bone.

FIG. 1 is a cross-sectional, side view of one embodiment of an artificial hip joint replacement system according to one aspect of the present invention implanted into a human acetabular bone. The artificial hip joint replacement system includes an acetabular portion 1, which includes cup 2. Cup 2 has a rigid portion 5 and elastic portions 6. Each of elastic portions 6 is attached to rigid portion 5. Cup 2 is received by (e.g., implanted into) acetabular bone 4. In the particular embodiment illustrated in FIG. 1, acetabular portion 1 includes shell 3 positioned between cup 2 and acetabular bone 4.

Shell 3 is an optional feature of the artificial hip joint replacement system of the present invention. According to one embodiment, when a shell is used it is attached to the cup or positioned between the subject's acetabular bone and the cup. In one embodiment, the shell is affixed to the cup, although this is not necessary. When the shell is affixed to the cup, this may be done by a variety of attachment methods including, without limitation, screws, an adhesion medium, or through a mechanical press-fit.

In the embodiment illustrated in FIG. 1, elastic portions 6 are attached to rigid portion 5 of cup 2. However, in other embodiments discussed infra, one or more elastic portions may be formed integrally with rigid portion 5 (see, e.g., FIG. 2).

The artificial hip joint replacement system illustrated in FIG. 1 also includes ball 7, which is received within cup 2 of acetabular portion 1. Ball 7 is in contact with elastic portions 6 of cup 2 when ball 7 is received within cup 2. Elastic portions 6 are positioned in cup 2 to cause expansion and allow contraction of clearance space 9 between ball 7 and rigid portion 5 of cup 2. Attached to ball 7 is femoral stem 8.

According to one embodiment, the cup is designed so that the clearance space is of variable size. In other words, the cup is designed so that its surface geometry deviates from perfect sphericity. Thus, the gap distance (space) between the surface of the ball received by the surface of the cup, when ball and cup centers are coincident, may not be uniform.

Figure 2:
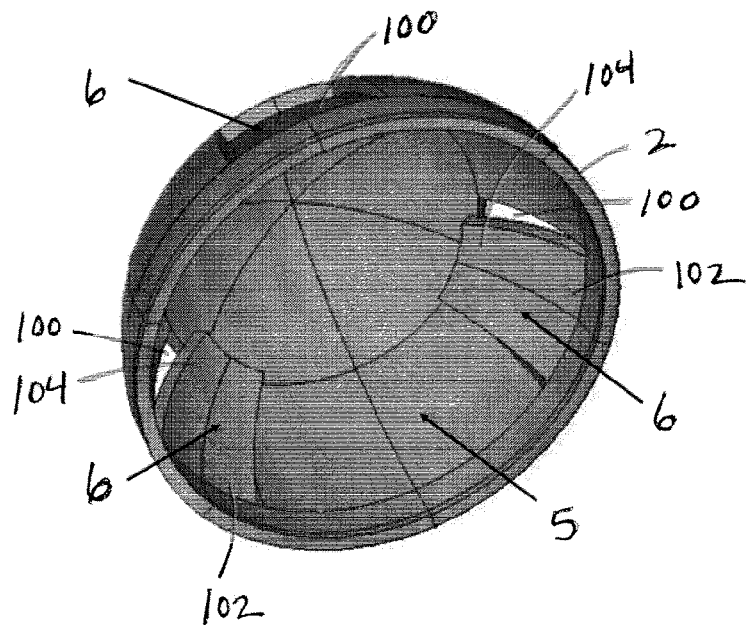
FIG. 2 is a perspective view of the underside of the cup of the artificial hip joint replacement system shown in FIG. 1. Elastic portions of the cup are fabricated as a continuous piece integrated with the rigid portion of the cup.

In FIG. 2, a perspective view of the underside of cup 2 from FIG. 1 is shown. As illustrated in FIG. 2, cup 2 has three elastic portions 6 which are fabricated as continuous pieces integrated with rigid portion 5 of cup 2. According to this embodiment, elastic portions 6 are elastic curved beams or fingers which, in their unstressed state, protrude into the ball-cup clearance space 9 (see FIG. 1) and contact the surface of ball 7 (see FIG. 1) which in turn is rigidly attached to femoral stem 8 (see FIG. 1). In other words, elastic portions 6 comprise elongate fingers or tabs each having a proximal end 102 attached to rigid portion 5 of cup 2 and a free end 104 distal from rigid portion 5. According to the particular embodiment illustrated in FIG. 2, elastic portions 6 are curved to receive the ball. In addition, rigid portion 5 comprises cut-away (or slotted) portions 100 proximate to elastic portions 6 which, as discussed infra, assist in the lubrication dynamics of the hip replacement system.

Other configurations of the elastic portions (or, as also referred to below, elastic elements and elastic material) of the artificial hip joint replacement system of the present invention are also contemplated by the present invention, as discussed in further detail below. Whatever their particular configuration is, the elastic portion(s) of the cup are positioned so that the ball and the rigid portion of the cup are farthest apart from one another during periods of low mechanical loads.

For example, another embodiment of the elastic portion(s) of the cup is illustrated in FIG. 3. According to this embodiment, elastic portion 16 comprises a curved beam having a circular cross-section in its unstressed state, which protrudes into the ball-cup clearance space 19 to contact a ball of the artificial hip joint replacement system. According to this embodiment, elastic portion 16 may be attached at one or more points on cup 12 or, alternatively, at one or more points on a shell to cup 12 (i.e., a shell positioned between cup 12 and a subject's acetabular bone). Cup 12 includes rigid portion 15 which has cut-away portion 100.

Figure 4C:
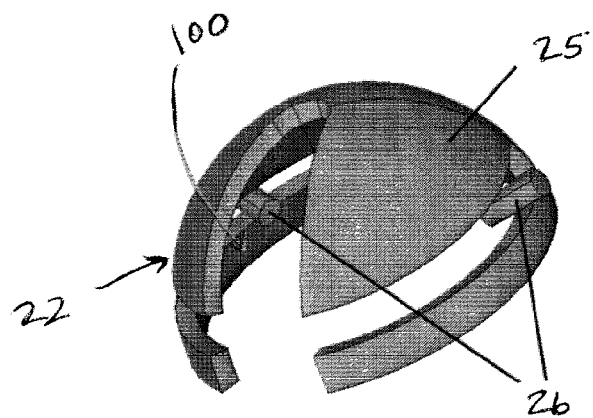

In yet another embodiment illustrated in FIGS. 4A-C, elastic cup portions 26 are in the form of short rod-like cylinders which protrude through openings in rigid portion 25 to enter clearance space 9 (see FIG. 1) to contact ball 27 (FIGS. 4A-B). In the particular embodiment shown in FIGS. 4A-C, rigid portion 25 of cup 22 has cut-away portion 100. According to this embodiment, and as discussed in more detail infra, cut-away portion 100 promotes lubrication to rigid portion 25 which is the load-carrying portion of cup 22.

Figure 5A:
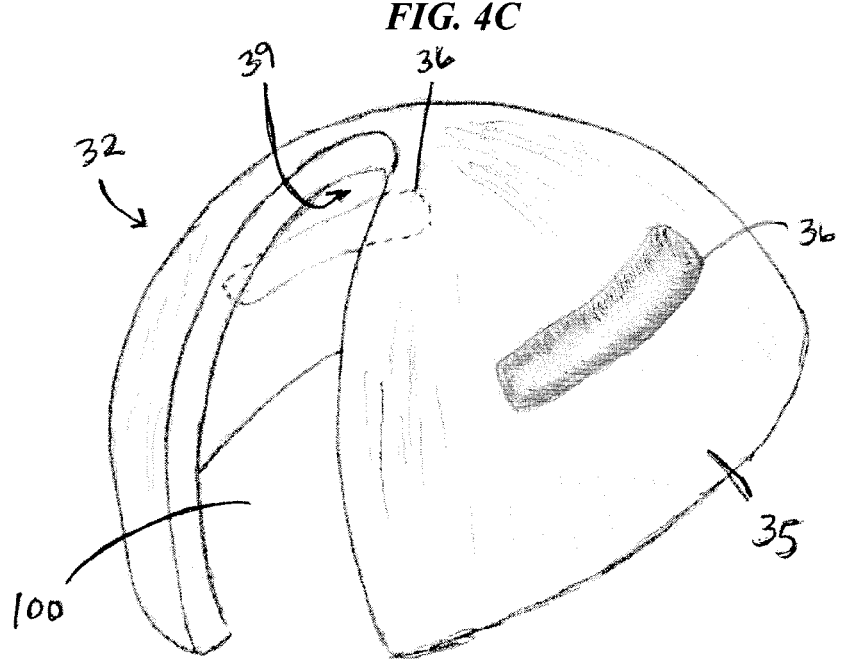
FIGS. 5A-B illustrate one embodiment of a cup of the acetabular portion of the artificial hip joint replacement system of the present invention. According to this embodiment, the cup includes a rigid portion and elastic portions formed in the rigid portion and which protrude into the ball-cup clearance space to contact a ball received within the cup.
Figure 5B:
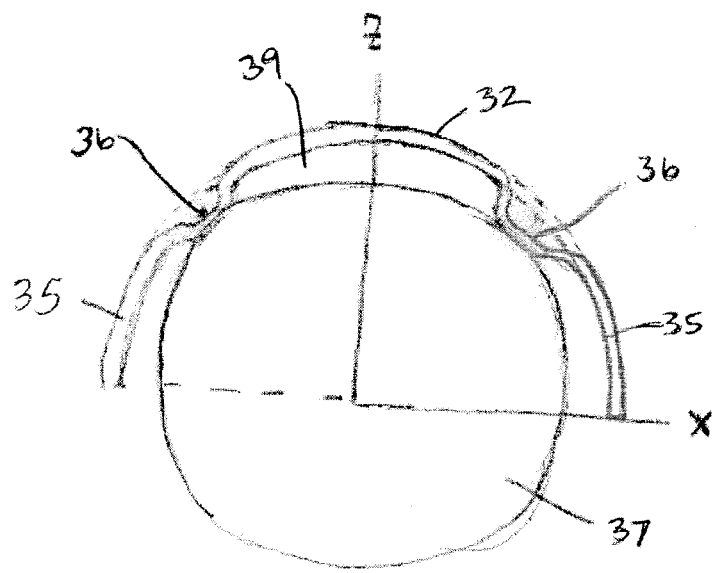

In still another embodiment illustrated in FIGS. 5A-B, cup 32 includes elastic portions 36 which protrude into clearance space 39 of the interior of cup 32. In the particular embodiment shown in FIGS. 5A-B, rigid portion 35 of cup 32 has cut-away portion 100. According to this embodiment, and as discussed in more detail infra, cut-away portion 100 promotes lubrication to rigid portion 35 which is the load-carrying portion of cup 32. FIG. 5B shows ball 37 positioned in cup 32 so that elastic portions 36 are in contact with ball 37.

Figure 6A:
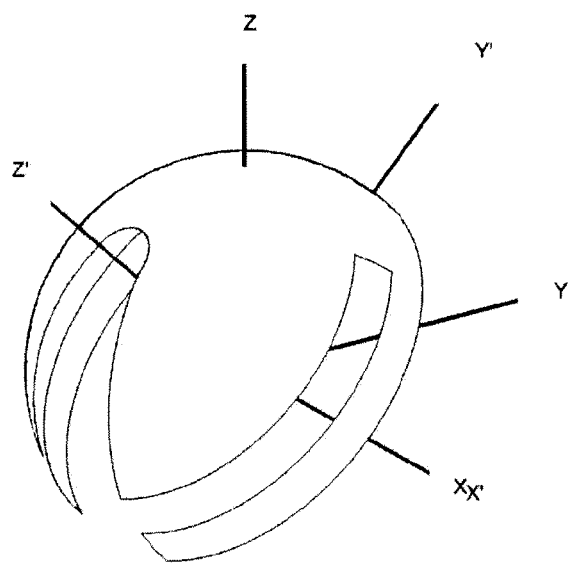
FIGS. 6A-B illustrate the surface geometry of one embodiment of a rigid portion of the cup of the acetabular portion of an artificial hip joint replacement system of the present invention.
Figure 6B:
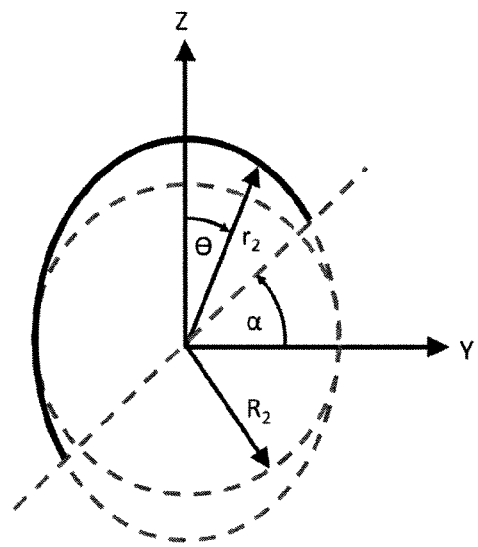

With reference now to FIGS. 6A-B, according to one embodiment of the present invention, the cup of the acetabular portion has a non-uniform radius. FIGS. 6A-B provide a schematic illustration of the rigid portion of the bearing cup surface of FIG. 3 relative to an X, Y, Z system axis affixed to the cup. The X, Y, and Z axes are oriented along the abduction-adduction, flexion-extension, and internal-external rotation axes of the hip joint, respectively. In one embodiment, the ball surface is perfectly spherical with (uniform) radius $R_1$, and the cup surface radius $r_2$ is defined by $$r_2 = R_2 + \delta \cos^2\theta$$

with ellipticity parameter $0 \leq \delta \ll R_2$ and $\cos\theta \approx Z/R_2$.

The cup surface can be visualized an ellipsoid of revolution with its major axis oriented along the (vertical) Z axis and which is cut by a plane oriented at the cup angle of inclination $\alpha$. The radial clearance between the ball and cup is then defined by $$C = C_0 + \delta \cos^2\theta$$

where nominal clearance $C_0 = R_2 - R_1$. The maximum radial clearance occurs along the major ellipsoidal axis situated along the vertical and not along the cup polar axis, in contradistinction to ellipsoidal cup studies by Wang et al., "Effect of Non-Spherical Bearing Geometry on Transient Elastohydrodynamic Lubrication in Metal-on-Metal Hip Joint Implants," *Proc. IMechE, Part J: Journal of Engineering Tribology* 221:379-389 (2007) and Wang et al., "Non-sphericity of Bearing Geometry and Lubrication in Hip Joint Replacements," *J. Tribol.* 131:031201 (2009), which are hereby incorporated by reference in their entirety.

According to the present invention, and with further reference to FIGS. 6A-B, the orientation of the elastic portion(s) of the cup is chosen so that the resultant force transmitted from the ball to the elastic portion(s) is directed along the vertical Z axis. Likewise, a cut-away portion of the rigid portion of the cup is designed to control the motion of the ball to lie along the vertical Z axis during the load-phase portion of the gait cycle (discussed infra, with reference to FIG. 7). If the cut-away (or slotted) portion is absent, squeeze film pressures generated on an essentially complete cup will tend to push the ball in the direction of the flexion-extension axis (Y axis) during the load-phase portion of the gait cycle. These considerations have been brought into account in selecting the particular design of the system of the present invention.

The primary lubrication mechanism relevant to the artificial hip joint replacement system of the present invention is squeeze-film action developed from normal approach of ball and cup surfaces and the creation of a pressure gradient to resupply lubricant to the bearing gap during normal separation of ball and cup surfaces. The squeeze-film action is intended to keep the rigid portions of the ball and cup surfaces separated from contact at all times over the entire gait cycle. The present invention accommodates but does not rely upon wedge-film lubricant action between the ball and rigid portion of the cup generated from the gait-cycle loads and kinematics. Sliding friction and boundary lubrication between the rigid and elastic surfaces are also created from the gait-cycle loads and kinematics. However, the portion of the external load carried by the elastic structures is substantially smaller than that carried by the lubricant squeeze-film so that the amount of wear generated between the rigid and elastic structures should be much smaller than that found in current designs.

Figure 7:
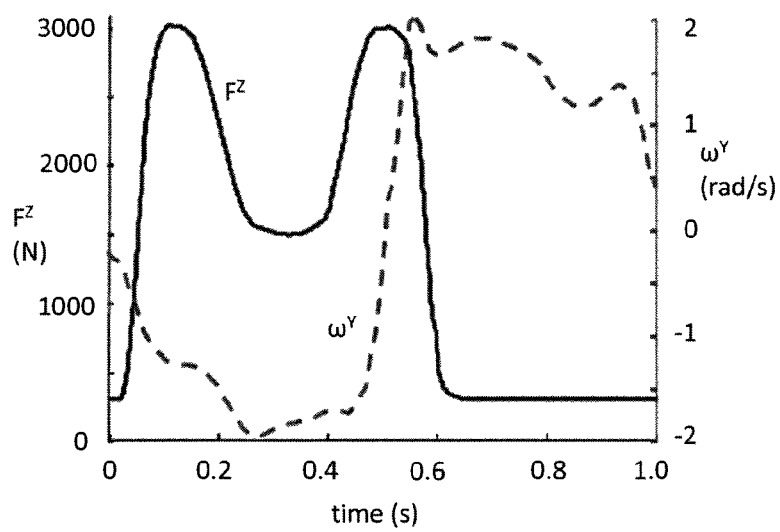
FIG. 7 is a graph showing the ISO 14242 duty cycle of the human gait.

Turning now to FIG. 7, the periodic time history of external load of the human gait cycle (International Standards Organization, ISO 14242-1: Implants for Surgery—Wear of Total Hip-Joint Prostheses—Part 1: Loading and Displacement Parameters for Wear Testing Machines and Corresponding Environmental Conditions for Test (2002), which is hereby incorporated by reference in its entirety) is shown. The external load components are transmitted from ball and cup and are referenced to a cartesian X,Y,Z coordinate frame attached to the cup where the Z axis is directed from the cup center through the cup's polar axis (see FIGS. 6A-B). The kinematics represent the angular velocity of the ball relative to cup with components referenced to the same cartesian X,Y,Z coordinate frame. The gait cycle is comprised of a load-phase portion, where the external load is variable in magnitude but does not reverse direction, and a swing-phase portion, where the external load is essentially zero.

At the start of the load-phase portion of the gait cycle, a clearance space or gap (see, e.g., space 9 of FIG. 1) exists between the ball surface and the rigid portion of the cup surface. At this instant, the available clearance is filled with synovial fluid. As the load-phase of the gait cycle progresses in time, the ball surface approaches the rigid surface of the cup. This motion causes the ball to contact and deform the elastic portion(s) which protrude into the clearance space (gap). The external load is carried primarily by pressure generated in the synovial fluid film as the synovial fluid is squeezed out of the diminishing clearance space. A portion of the external load is also transmitted directly through deformation of the elastic portion(s), and the magnitude of the load carried by the elastic portion(s) steadily increases as the ball moves closer to the interior rigid portion of the cup. However, the spring rate of the elastic portion(s) is chosen so that only a very small amount of the external load is carried by the elastic portion(s) by the time that the end of the load amount of the gait cycle is reached. During the load-phase of the gait cycle, essentially all the external load is transmitted from the ball to the rigid portion of the cup through the lubricant film.

During the swing-phase portion of the gait cycle, the external load is essentially absent (although some load does still exist), and the ball surface is pushed away from the rigid portion of the cup surface by the spring load created by deformation of the elastic portion(s). Also during this swing phase, separation of cup and ball surfaces results in cavitation of the synovial fluid within the available clearance space. Pressures in the cavitation region are generally believed to be subambient (Hays & Feiten, "Cavities Between Moving Parallel Plates," *In Cavitation in Real Liquids*, Elsevier, 1964, pp. 122-137; and Boedo, "Mass Conserving Cavitation Effects in Squeeze-film Journal Bearings Subjected to Sinusoidal Loads," *STLE Tribology Transactions*, vol. 54, 2011, pp. 21-35, which are hereby incorporated by reference in their entirety) such that a pressure difference exists between the ambient pressure at the bearing edges and the cavitation region. This pressure gradient provides a mechanism to supply synovial fluid back into the bearing region during the swing phase when the ball surface and the rigid portion of the cup surface are undergoing normal separation. At the end of the swing phase of the gait cycle, the ball has been displaced by the elastic portion(s), and an available lubricant supply once again exists in the created clearance space.

This process of normal ball-cup surface approach in the load phase and normal ball-cup surface separation in the swing phase repeats with the periodic gait cycle. In this manner, substantially thicker fluid films can be retained by "squeeze film" action than would be generated by "wedge-film" action alone. These thicker films reduce the likelihood of ball-cup surface asperity contact which in turn reduces the probability for wear.

Figure 30:
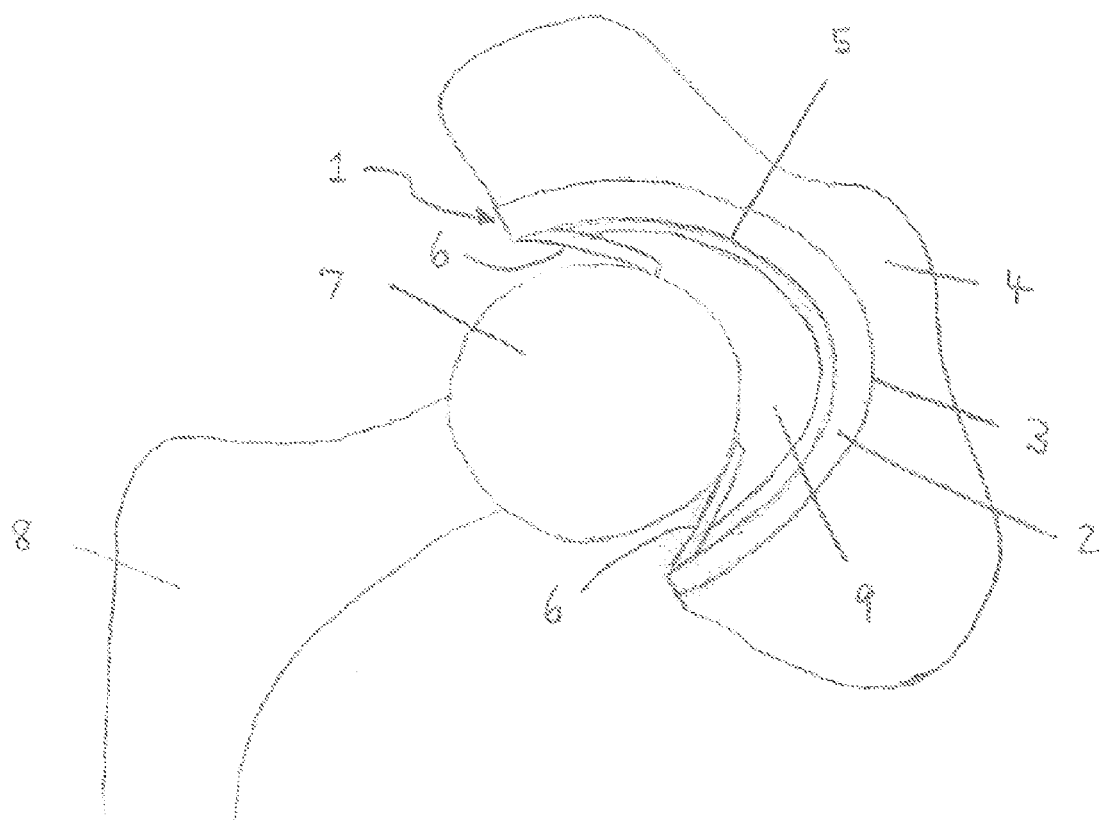
FIG. 30 is a cross-sectional, side view of one embodiment of an artificial hip joint replacement system of the present invention, where the rigid portion of the cup has an ellipsoidal shape and the ball has a spherical shape.
Figure 31:
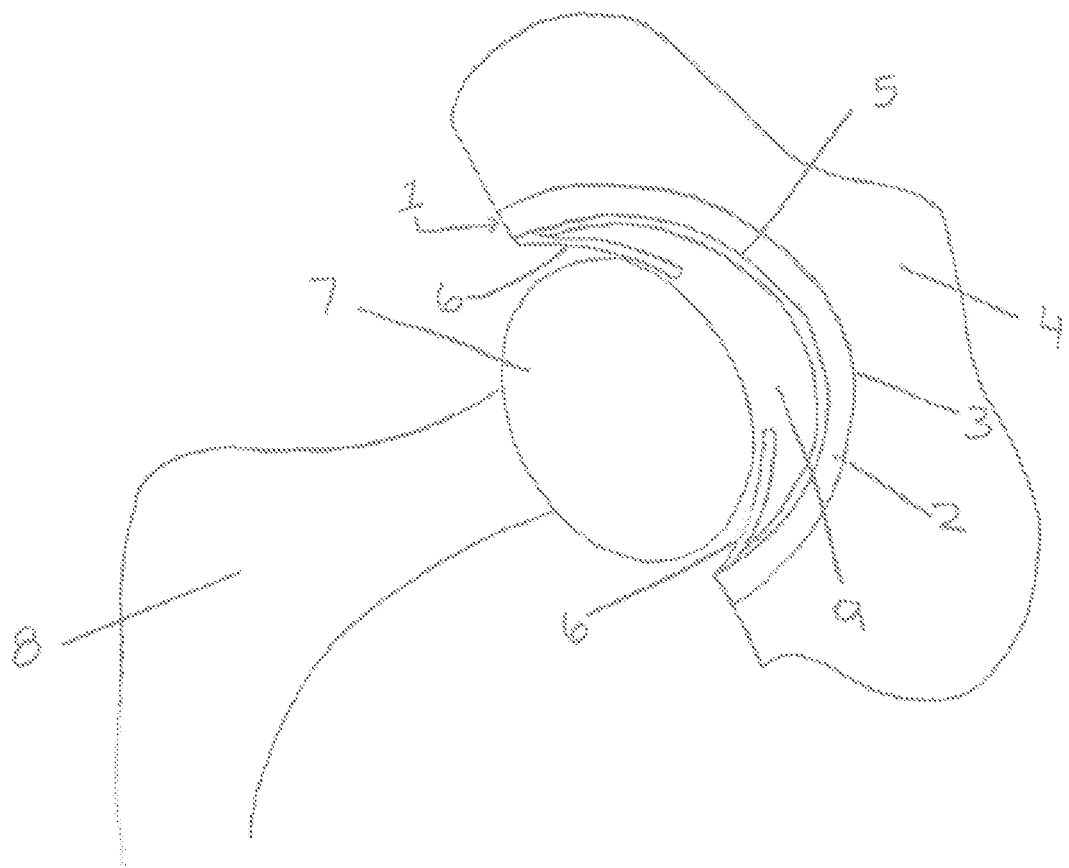
FIG. 31 is a cross-sectional, side view of one embodiment of an artificial hip joint replacement system of the present invention, where the rigid portion of the cup has a spherical shape and the ball has an ellipsoidal shape.

According to one embodiment of this aspect of the present invention, the rigid portion of the cup is non-spherical (e.g., has an ellipsoidal shape) (FIG. 30). According to this embodiment, the ball of the system is either spherical or non-spherical. In another embodiment, the rigid portion of the cup is spherical and the ball is non-spherical (FIG. 31).

Another aspect of the present invention also relates to an artificial hip joint replacement system. This system includes an acetabular portion comprising a cup suitable to be received by a subject's acetabular bone. The system also includes a ball comprising a rigid portion and an elastic portion attached to the rigid portion. The ball is received within the cup with the elastic portion of the ball being in contact with the cup. Also included in the system is a femoral stem attached to said ball. The elastic portion of the ball is positioned to cause expansion and allow contraction of a space between the ball and the cup so they are farthest apart from one another during periods of low mechanical loads.

Figure 8:
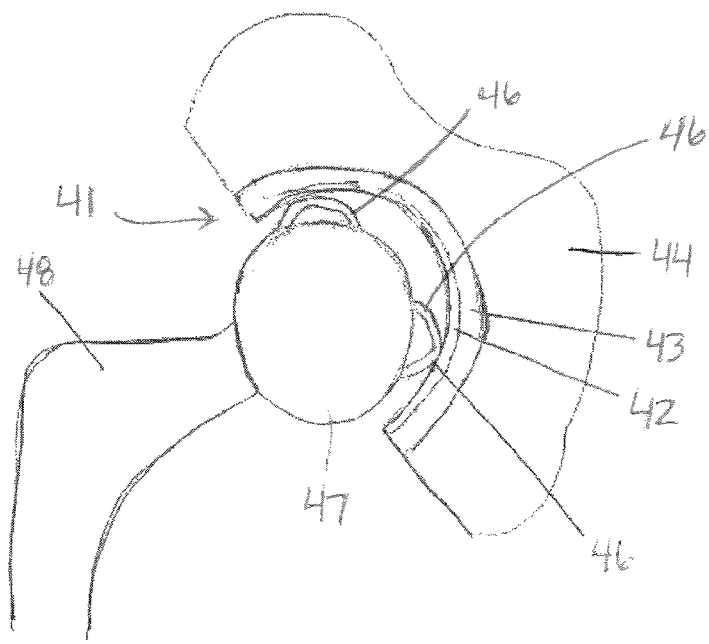
FIG. 8 is a cross-sectional, side view of one embodiment of an artificial hip joint replacement system of the present invention implanted into a human acetabular bone.

One embodiment of this aspect of the present invention is illustrated in FIG. 8, which is a cross-sectional side view of an artificial hip replacement system implanted into the acetabular bone of a subject. The hip joint replacement system includes acetabular portion 41 comprising cup 42 and shell 43 (optional) implanted into acetabular bone 44. Ball 47 is received within cup 42. Ball 47 includes elastic elements 46 attached to ball 47. Ball 47 is attached to femoral stem 48.

According to this embodiment of the present invention, elastic elements 46 are attached to ball 47. As discussed above with respect to elastic portion(s) attached to the cup, elastic elements 46 may be attached to ball 47 or formed as part of ball 47.

As discussed supra with respect to elastic portion(s) formed on the acetabular portion, whatever the particular configuration of the elastic element(s) formed on the ball according to this aspect of the present invention, the elastic element(s) are configured so that the ball and the cup are farthest apart from one another during periods of low mechanical loads.

Figure 9:
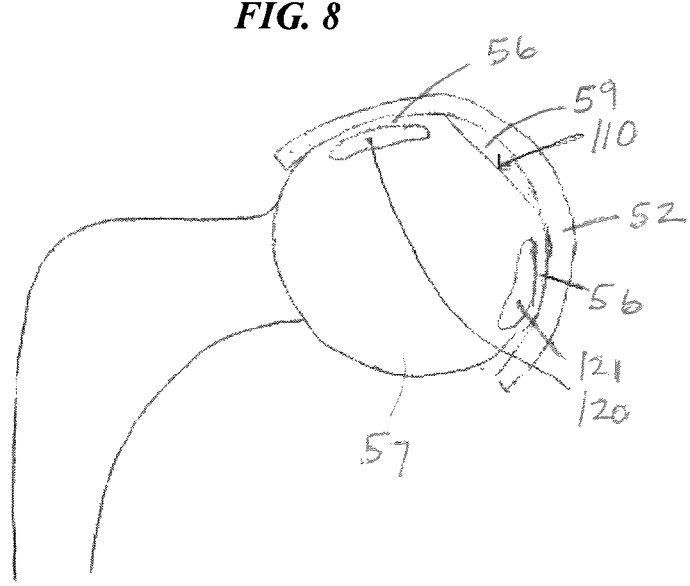
FIG. 9 is an alternative embodiment of the ball component of the artificial hip joint replacement system of FIG. 8.

Another embodiment of this aspect of the present invention is illustrated in FIG. 9. This figure shows an artificial hip replacement system that includes ball 57 which has a portion of material removed to avoid contact with the cup at a particular spot 110. Elastic elements 56 are formed as thin elastic layers on the edge of ball 57, which are formed by removal of material at portions 120 and 121. Again, this particular configuration is so that the elastic elements 56 of ball 57 cause expansion and allow contraction of a space 59 between ball 57 and cup 52 so they are farthest apart from one another during periods of low mechanical loads.

Figure 10A:
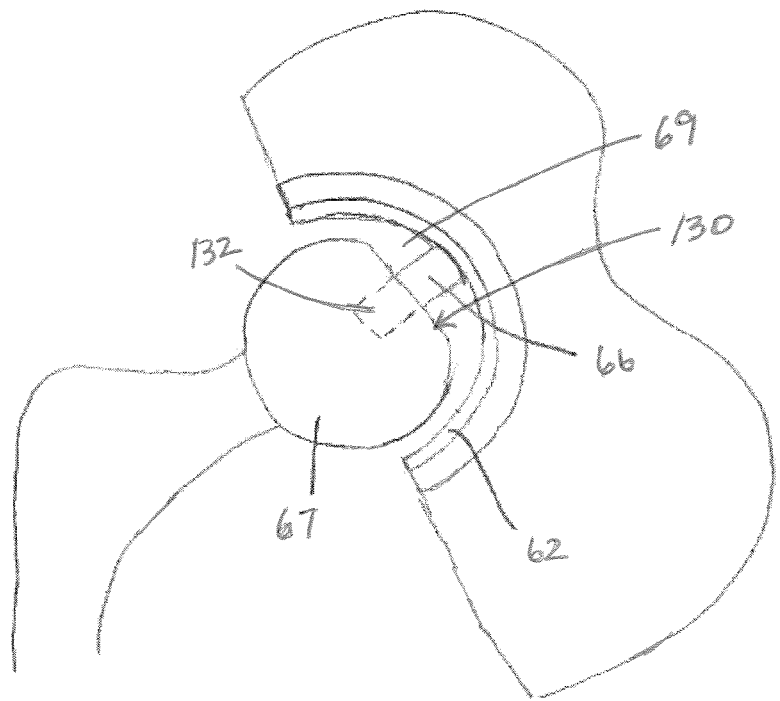
FIGS. 10A-C illustrate one embodiment of the artificial hip joint replacement system of the present invention.
Figure 10B:
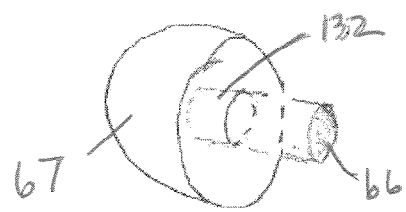
Figure 10C:
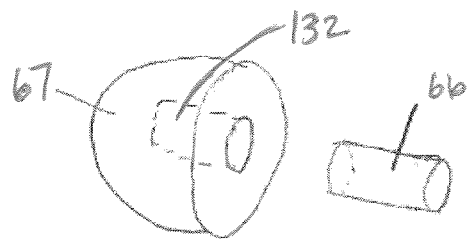

Yet another embodiment of this aspect of the present invention is illustrated in FIGS. 10A-C. In the artificial hip joint replacement system illustrated in FIGS. 10A-C, ball 67 has a flattened face 130 and socket 132 formed into flattened face 130. Socket 132 is capable of receiving elastic element 66 so as to cause expansion and allow contraction of a space 69 between ball 67 and cup 62 so they are farthest apart from one another during periods of low mechanical loads.

Figure 11:
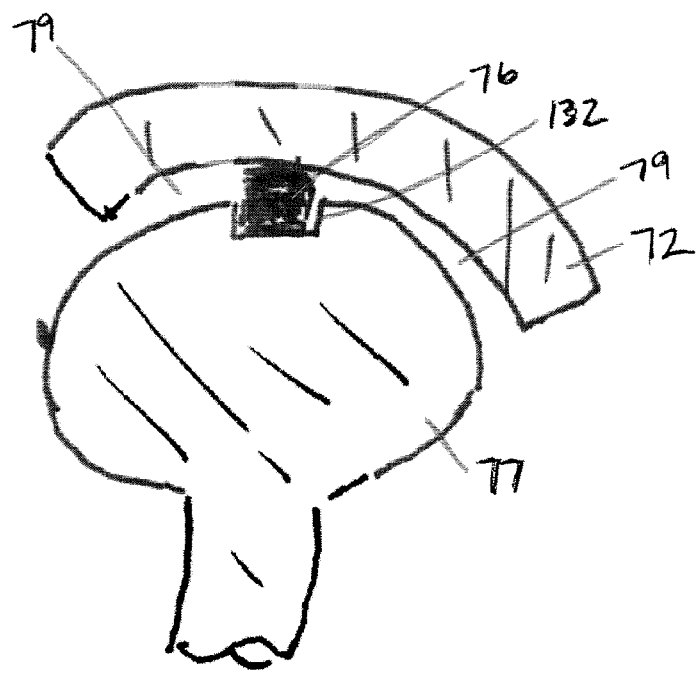
FIG. 11 is a cross-sectional view of one embodiment of the cup and ball components of the artificial hip joint replacement system of the present invention which includes an ellipsoidal-shaped ball component comprising a socket in which an elastic element is seated.

In the particular embodiment illustrated in FIG. 11, ball 77 has an ellipsoid shape with socket 132 formed into ball 77 to receive elastic element or elastic material 76. Again, socket 132 is capable of receiving elastic element 76 so as to cause expansion and allow contraction of a space 79 between ball 77 and the cup 72 so they are farthest apart from one another during periods of low mechanical loads.

A further aspect of the present invention relates to an artificial hip joint replacement system. This system includes an acetabular portion comprising a cup suitable to be received by a subject's acetabular bone. The system also includes a ball received within the cup and an elastic element in contact with the ball and the cup. The elastic element is positioned to cause expansion and allow contraction of a space between the ball and the cup so they are farthest apart from one another during periods of low mechanical loads. The system also includes a femoral stem attached to the ball.

According to one embodiment of this aspect of the present invention, the elastic element is attached to the ball. In another embodiment, the elastic element is attached to the cup. In yet another embodiment, the elastic element is attached to neither the cup nor the ball. In still another embodiment, one elastic element is attached to the cup and another elastic element is attached to the ball.

Figure 12:
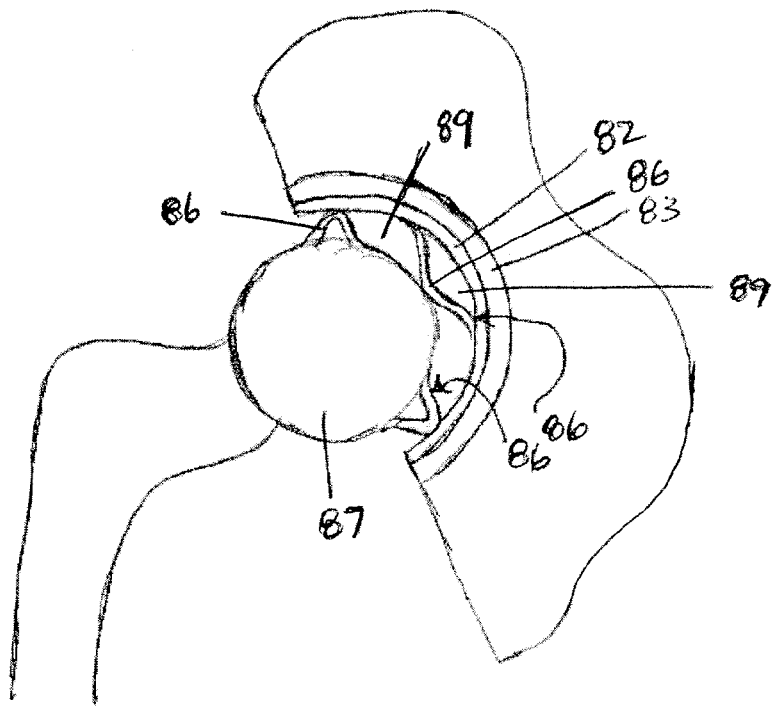
FIG. 12 is a cross-sectional, side view of one embodiment of an artificial hip joint replacement system of the present invention implanted into a human acetabular bone. Elastic elements are formed on both the ball and the cup of the acetabular portions of the system.

One embodiment of this aspect of the present invention is illustrated in FIG. 12. FIG. 12 is a cross-sectional side view of an artificial hip joint replacement system of the present invention implanted into a subject's acetabular bone. According to this embodiment, elastic elements 86 are formed on ball 87 and cup 82. Elastic elements 86 are positioned to cause expansion and allow contraction of space 89 between ball 87 and cup 82 so they are farthest apart from one another during periods of low mechanical loads.

Figure 13:
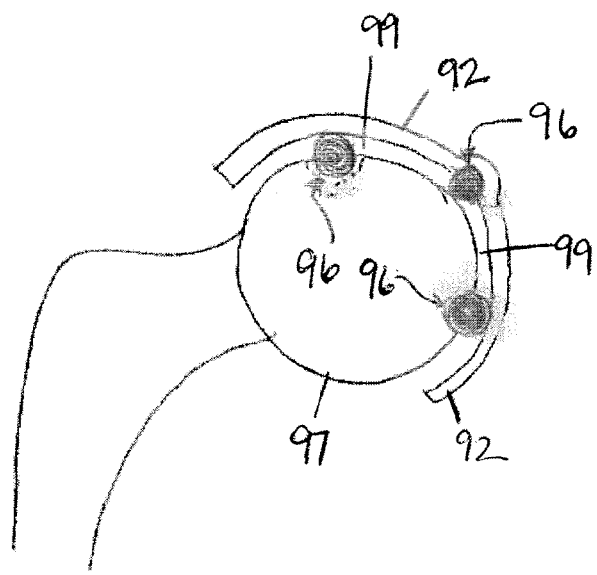
FIG. 13 is a cross-sectional, side view of one embodiment of the cup, ball, and femoral stem components an artificial hip joint replacement system of the present invention which include elastomeric material attached to the cup and to the ball.

In the embodiment illustrated in FIG. 13, elastomeric material 96 is attached to both cup 92 and ball 97. Elastic material 96 are positioned to cause expansion and allow contraction of space 99 between ball 97 and cup 92 so they are farthest apart from one another during periods of low mechanical loads.

According to another embodiment, the elastic portion(s) may be arbitrarily situated, for example, in the polar region of the cup. In this embodiment, the elastic portion(s) contacts the ball in the polar region of the cup, and the rigid portion of the cup which carries the lubricant film and which supports the external gait cycle load would be situated outside of the polar region. In addition, the elastic portion(s) can be positioned asymmetrically with respect to the polar cup axis, and the geometrical configuration of each elastic portion(s) does not need to be identical with each other.

According to the present invention, the elastic portion(s) of the system can vary in number and location, are considerably more compliant than the remainder of the system, protrude into the clearance space, and provide a mechanical means of separating the rigid portions of the ball and cup surfaces during the swing-phase of the gait cycle.

The components of the artificial hip joint replacement system of the present invention may be constructed of a variety of materials well known to those of ordinary skill in the art. The components of the system may be constructed of the same or different materials, except the elastic portion(s) (or elastic elements or elastic material) of the system is typically not constructed of the same material as the other components of the system.

Suitable materials for the components other than the elastic portion(s) include a variety of durable materials now known or later to be discovered as suitable for human implants. Suitable materials include, without limitation, metallic, ceramic, or plastic materials. According to one embodiment, the components of the system are made from polymeric (e.g., high molecular weight polyethylenes), metallic (e.g., cobalt chrome alloys, titanium alloys, etc.), and ceramic materials. When a polymeric material is used, it might be used as the liner of a component (e.g., the cup). However, the system of the present invention lends itself to the use of hard materials which are less prone to wear, such as metallic and ceramic materials. For example, the bearing surfaces (i.e., cup and ball) might be made from metallic materials or ceramic materials. Often, it will be preferred for the materials of the bearing surfaces to be different, especially by using materials of which one is harder than the other. The components can be formed from two materials, for example by the application of a surface layer of a first material onto a substrate formed from a second material. For example, a layer of a ceramic material might be provided on a metallic substrate.

According to one embodiment of the present invention, the rigid portion of the cup has some inherent elasticity from its material properties, and the denotation of this region as "rigid" is meant only to serve as a reference to the elastic portion(s) of the cup which are considerably more compliant.

Suitable materials for forming the elastic portion(s) of the system of the present invention include, without limitation, metallic, ceramic, or plastic materials. According to one embodiment, the components of the system are made from polymeric (e.g., ultra high molecular weight polyethylenes). According to a different embodiment, the components of the system are made from a metallic alloy (e.g., Arcam Ti-6Al4V-ELI).

The acetabular portion of the artificial hip join replacement system of the present invention may be implanted into a subject's acetabular bone by a variety of methods, including attaching the cup (and, optionally, a shell) to the acetabular bone. When it is attached to the acetabular bone, the cup may be attached by any of a variety of methods used by orthopedic surgeons to implant joint prosthetics, including hip joint replacement systems. For example, attachment may involve the use of screws, a nut and bolt combination, pins, threaded parts (e.g., threads on a bone contact portion of the cup or shell), an adhesion medium, or a mechanical press-fit. Attachment methods of the acetabular portion are described, for example, in U.S. Pat. No. 6,517,583 to Pope et al., which is hereby incorporated by reference in its entirety.

The bone contact portion of the acetabular portion of the joint replacement system of the present invention may optionally include one or more surface coatings to encourage bone growth, such as those described in U.S. Pat. No. 6,517,583 to Pope et al., which is hereby incorporated by reference in its entirety.

In one embodiment of the acetabular portion in which a shell is used, the cup and the shell are formed as an integrated piece instead of two separately assembled components, as exemplified in U.S. Pat. No. 4,531,243 to Weber et al., which is hereby incorporated by reference in its entirety.

EXAMPLES

The following examples are provided to illustrate embodiments of the present invention but are by no means intended to limit its scope.

Example 1

An Elastic Squeeze Film Total Hip Replacement

Features of the Proposed Design

FIGS. 4A-C show anterior and lateral exploded views of one possible embodiment of the new artificial hip joint as installed in the human body. The acetabular cup is divided into "elastic" and "rigid" elements. Elastic columns in their unstressed state protrude into the ball-cup clearance space and maintain contact with the spherical ball surface over the entire gait cycle. A thin lubricant film is situated between the ball surface and the rigid portion of the cup. (Though the rigid portion of the cup has some inherent compliance, its denotation is meant only to distinguish from the elastic elements which are considerably more compliant.)

The elastic elements can be fabricated as a continuous piece integrated with the rigid portion of the cup or affixed to the shell backing. The rigid portion of the cup is attached to the shell in the usual manner through connections such as screws, an adhesion medium, or a mechanical press-fit.

As explored in the next paragraph, a complete (liquid) lubricant film is presumed to fill the available clearance space between the ball surface and the rigid portion of the cup surface at the start of the stance phase of the gait cycle. Throughout the stance phase, the major portion of the external load is carried by the lubricant film transmitted to the cup through squeeze-film action generated by the normal approach of the ball and cup surfaces. The remaining minor portion of the external load is transmitted through direct contact of the elastic elements and the ball.

During the swing phase, the external load becomes smaller than the force from the elastic elements, and the ball and cup surfaces undergo normal separation, resulting in cavitation of the lubricant film within the available clearance space. Pressures in the cavitation region are generally believed to be subambient (Unsworth, "Cavitation in Human Joints," In *Cavitation and Related Phenomena in Lubrication*, D. Dowson et al. (Eds.), IMechE Publications Ltd., pp. 119-127 (1975), which is hereby incorporated by reference in its entirety), and the resulting pressure difference relative to the cup edges (at ambient pressure) provides a mechanism to supply lubricant back into the bearing region. At the end of the swing-phase, the ball has been displaced by the elastic elements, and a complete lubricant film is once again available in the created clearance space.

This process of normal ball-cup surface approach during the stance phase and normal ball-cup surface separation during the swing phase repeats with the periodic gait cycle.

FIG. 2A shows a schematic of the rigid portion of the bearing cup surface. System X', Y', Z' axes are affixed to the cup with the Z' axis oriented along the cup polar axis. System X, Y, and Z axes are oriented along the abduction-adduction, flexion-extension, and internal-external rotation axes of the hip joint, respectively. The cup geometry is symmetric with respect to the Y'-Z' plane. Slots control film load direction and promote lubrication transport to the load-carrying portion of the cup. As illustrated in FIG. 2B, the cup surface radius $r_2$ is defined by $$r_2 = R_2 + \delta \cos^2 \theta \qquad (1)$$

with nominal cup radius $R_2$ and ellipticity parameter $0 \leq \delta \ll R_2$. The cup surface profile very closely approximates an ellipsoid of revolution with its major axis oriented along the (vertical) Z axis and cut by a plane oriented at the cup inclination angle α (FIG. 2B).

Assuming a perfectly spherical ball with radius $R_1$, the radial clearance between the ball and cup is thus defined by $$C = C_0 + \delta \cos^2\theta \quad (2)$$

with nominal clearance $C_0 = R_2 - R_1$. The maximum radial clearance occurs along the major ellipsoidal axis Z and not along the cup polar axis Z', in contradistinction to ellipsoidal cup studies by Wang et al., "Effect of Non-Spherical Bearing Geometry on Transient Elastohydrodynamic Lubrication in Metal-on-Metal Hip Joint Implants," *Proc. IMechE, Part J: Journal of Engineering Tribology* 221:379-389 (2007); Wang et al., "Nonsphericity of Bearing Geometry and Lubrication in Hip Joint Replacements," *J. Tribol.* 131:031201 (2009), which are hereby incorporated by reference in their entirety.

The film thickness distribution at time t is given by $$h(t) = C - e(t) \cdot n \quad (3)$$

in terms of ball eccentricity (position) vector e with system components $e^X$, $e^Y$, $e^Z$, and surface normal vector n with system components $n^X \approx X/R_2$, $n^Y \approx Y/R_2$, $n^Z \approx Z/R_2$.

For ball motion along the Z axis, ball and cup approach point contact situated at $\theta = 0$ for ellipticity specifications $0 \leq \delta < C_0$. The contact geometry bifurcates from point contact to circular line contact at $\delta = C_0$ with radius of increasing ellipticity for $\delta > C_0$.

Stance Phase Simulation Method

The numerical simulations employ a mass-conserving finite-element cavitation algorithm (Kumar and Booker, "A Finite Element Cavitation Algorithm," *J. Tribol.* 113:276-286 (1991); Boedo and Booker, "Finite Element Analysis of Elastic Engine Bearing Lubrication: Application," *Revue Européenne des Éléments Finis* 10:725-740 (2001); Booker and Boedo, "Finite Element Analysis of Elastic Engine Bearing Lubrication: Theory," Revue Européenne des Éléments Finis 10:705-724 (2001), which are hereby incorporated by reference in their entirety) with components of ball eccentricity e and nodal density (denoted as $\{\rho\}$) as state variables.

FIG. 7 shows the periodic time history of external load F (ball to cup) and ball angular velocity ω which represent the generally accepted ISO 14242 standard (International Standards Organization, ISO 14242-1: Implants for Surgery—Wear of Total Hip-Joint Prostheses—Part 1: Loading and Displacement Parameters for Wear Testing Machines and Corresponding Environmental Conditions for Test (2002), which is hereby incorporated by reference in its entirety) employed in hip simulator wear testing. The planar gait cycle load is positive in the vertical direction (Z axis) and is comprised of a double-peak stance-phase load of magnitude 3000 N and a constant swing-phase load with magnitude 300 N. The ball angular velocity history is specified only about the Y axis and represents flexion-extension kinematic action. While the full duty cycle of ISO 14242 is two-dimensional with a period of 1.0 s, the ball is not restricted to planar linear motion.

Figure 14:
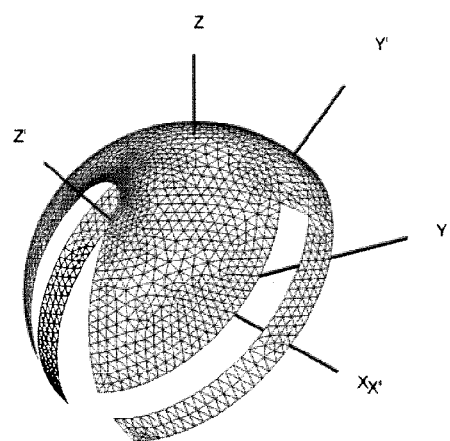
FIG. 14 is a spatial view of one embodiment of the lubricant film mesh (i.e., synovial fluid) existing between the acetabular portion and the ball of one embodiment of an artificial hip joint replacement system of the present invention.

FIG. 14 shows a spatial view of the lubricant film associated with the rigid portion of the cup surface. The film is represented by a contiguous set of three-noded planar triangular finite elements connected at a discrete set of nodes whose spatial coordinates are specified relative to the system X, Y, Z axis attached to the cup. Prescribed ambient (zero gauge) pressure and liquid density are specified for nodes situated along the mesh boundary.

The device of approximating a spherical lubricant film by planar triangular elements offers great flexibility in meshing irregular surface regions and avoids numerical difficulties associated with spherical coordinates. Formulation details and validation studies are provided in Example 2.

Figure 15:
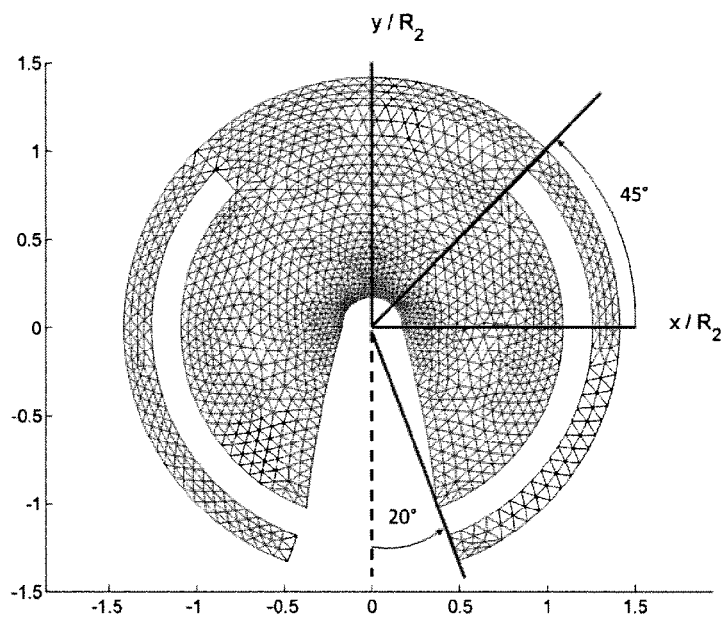
FIG. 15 is a projected view graph of the lubricant film mesh existing between the acetabular portion and the ball of one embodiment of an artificial hip joint replacement system of the present invention.

FIG. 15 shows a view of the film mesh projected onto an x, y plane normal to cup polar axis Z' and oriented such that the x-X' and y-Y' axes pairs are parallel. The mapping of elements from the hemisphere to the plane is constructed so that element areas of the hemisphere and plane are proportional (in this case equal), thus minimizing element distortion along the bearing edges. Mapping details are provided in Example 3.

Ball motion and fluid density evolution are governed by state rate relations of the general form $$de/dt = f(e, \{\rho\}, t) \quad (4)$$

$$d\{\rho\}/dt = \{g\}(e, \{\rho\}, t) \quad (5)$$

with initial state $$e(t_0) = e_0 \quad (6)$$

$$\{\rho(t_0)\} = \{\rho_0\} \quad (7)$$

These relations incorporate the quasistatic force balance $$F_{film} = F(t) - F_{elast}(e) \quad (8)$$

where $F_{film}$ and $F_{elast}$ are film load and elastic load vectors, respectively, transmitted from ball to cup. For the geometry of FIGS. 4A-C, the two elastic elements are designed to provide a nearly constant resultant elastic load of 350 N in the Z direction when ball eccentricity is $e^Z > 0$. Elastic load components in the X and Y directions are assumed to be negligibly small. Elastic design details are provided in Example 4.

The isoviscous fluid model employed in these studies takes on viscosity values between 1 mPa·s and 2.5 mPa·s to represent a range of rheological properties of periprosthetic synovial fluid at the high shear rates encountered during walking (Cooke et al., "The Rheology of Synovial Fluid and Some Potential Synthetic Lubricants for Degenerate Synovial Joints," *Engineering in Medicine* 7:66-72 (1978); Yao et al., "The Influence of Lubricant and Material on Polymer/CoCr Sliding Friction," *Wear* 255:780-784 (2003); Wang et al., "Transient Elastohydrodynamic Lubrication of Hip Joint Implants," *J. Tribol.* 130:011007 (2008); Mattei et al., "Lubrication and Wear Modelling of Artificial Hip Joints: A Review," *Tribology International* 44:532-549 (2011), which are hereby incorporated by reference in their entirety). The cavitation algorithm requires the specification of a cavitation threshold parameter which is here set to 0 gauge pressure (with gauge values taken relative to ambient pressure). For the studies here, essentially identical results are obtained using a cavitation threshold pressure at the generally accepted lower bound of −101 kPa. The piezoviscous behavior of synovial fluid is also assumed to be negligible at film pressures encountered in the joint (Mattei et al., "Lubrication and Wear Modelling of Artificial Hip Joints: A Review," *Tribology International* 44:532-549 (2011), which is hereby incorporated by reference in its entirety).

With external and elastic loads acting along the Z axis, the stance-phase simulation is started when $F^Z - F^Z_{elast} > 0$ ($t_0 = 0.03$ s) along with an initially complete liquid film and initially concentric ball and cup. The stance-phase simulation ends when $F^Z - F^Z_{elast} < 0$ which in this case occurs at t=0.63 s. The simulation employs an implicit variable-step numerical integration routine such that relative and absolute local errors on computed ball eccentricity components are less than $1 \times 10^{-8}$ and $1 \times 10^{-12}$ m, respectively.

Stance Phase Simulation Results

Figure 16A:
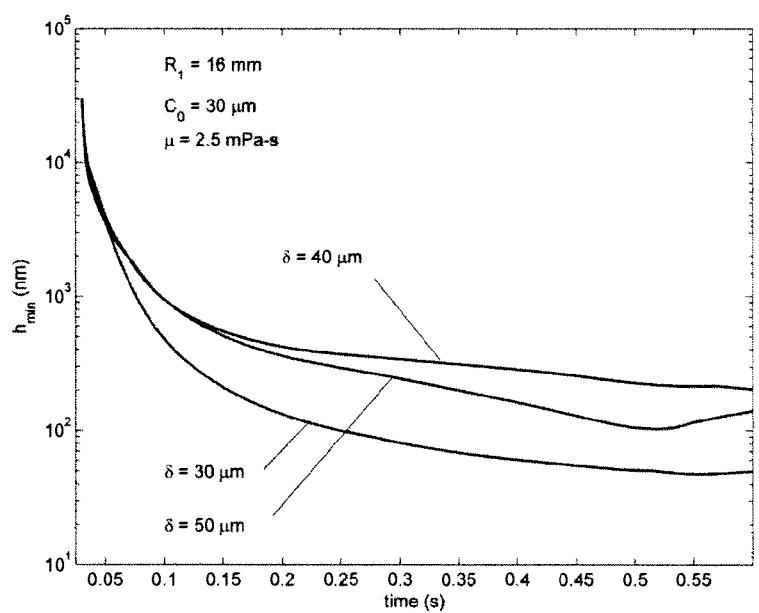
FIGS. 16A-B are line graphs showing the effect of ellipticity of the cup of the acetabular portion according to one embodiment of an artificial hip joint replacement system of the present invention on time histories of minimum film thickness (FIG. 16A) and maximum film pressure (FIG. 16B).
Figure 16B:
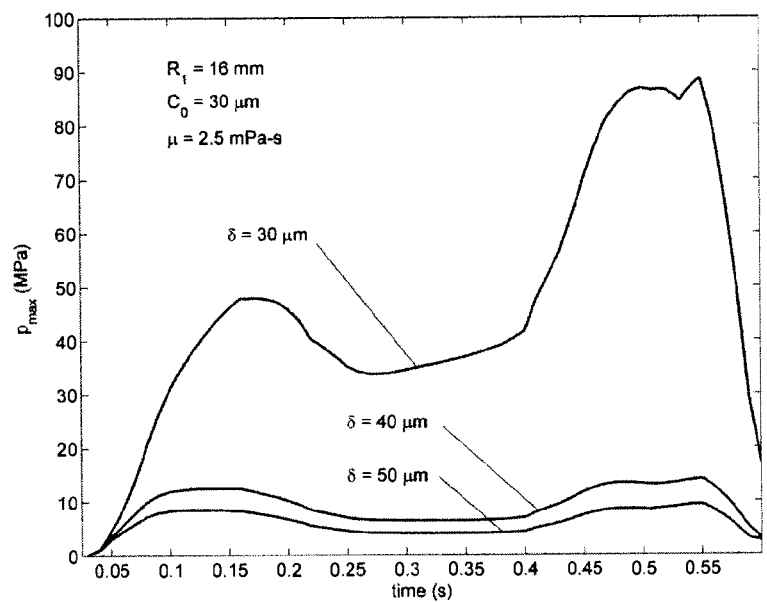

FIGS. 16A-B show that ellipticity magnitude can have a substantial effect on the resulting time histories of minimum film thickness and maximum film pressure, assuming ball and cup are initially concentric. Cup inclination angle α is fixed to 45 degrees throughout this study. With ball radius $R_1$=16 mm and nominal radial clearance $C_0$=30 μm, the minimum film thickness values for ellipticity specifications $\delta > C_0$ fall well within the full-film lubrication regime for metal-on-metal and ceramic-on-ceramic implants. The maximum film pressure is much smaller than those encountered in EHD hip joint studies and strongly suggests that rigid cup surface assumptions are justifiable here.

Figure 17A:
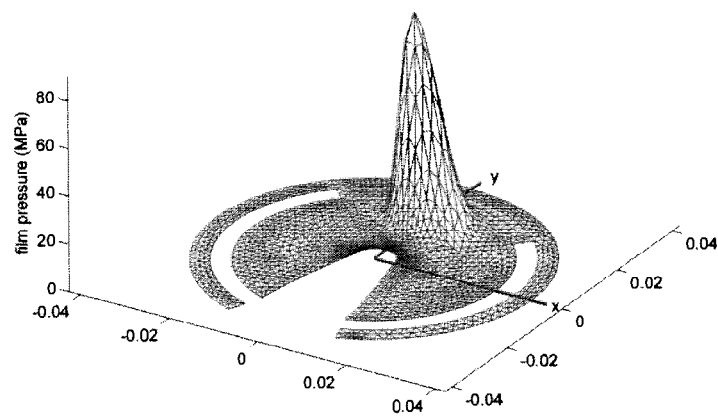
FIGS. 17A-C are graphs showing pressure distributions at t=0.5 s: $R_1$=16 mm, $\mu$=2.5 mPa·s. In each of these graphs, the time t refers to the instant in the gait cycle of FIG. 7, $\mu$ is the fluid viscosity, $R_1$ refers to ball radius, and $C_0$ refers to nominal radial clearance as described below. In each of these figures, the pressure is that carried by the lubricant film at the given instant in time, and the pressure is plotted in a projected view similar to FIG. 15.
Figure 17B:
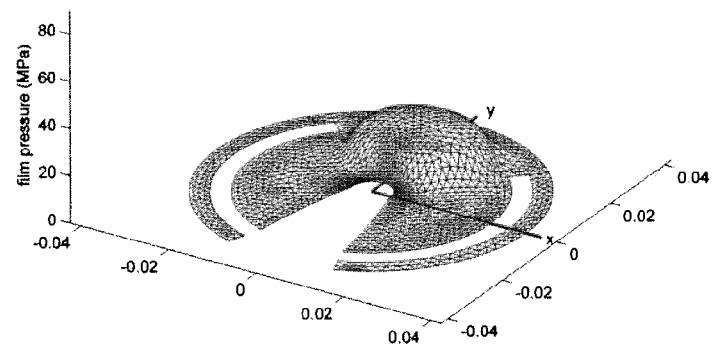
Figure 17C:
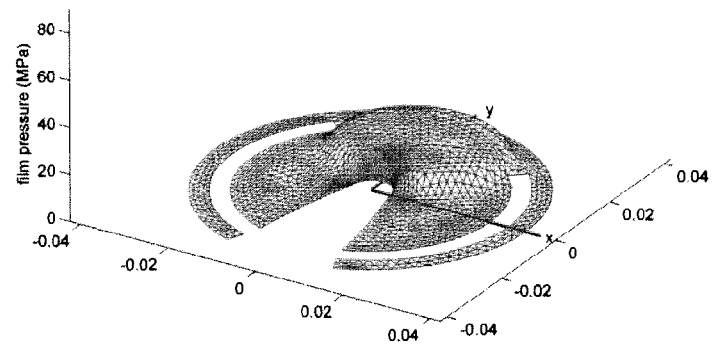

FIGS. 17A-C show spatial distributions of film pressure at time t=0.5 s corresponding to the time history curves of FIGS. 16A-B. For ellipticity specifications $\delta > C_0$, the ball and cup surfaces approach circular line contact, with the result that film pressures are substantially redistributed and reduced to a nearly uniform value over the polar region of the cup.

FIGS. 8A-B and FIGS. 19A-B show extrema values of minimum thickness and maximum film pressure encountered over the stance phase for specified values of nominal radial clearance and ellipticity. The selected clearance and ellipticity specifications fall within current manufacturing ranges for metal-on-metal and ceramic-on-ceramic implants, and optimal minimum film thickness values correspond to a full-film lubrication regime for these bearing materials based on reported roughness values (Mattei et al., "Lubrication and Wear Modelling of Artificial Hip Joints: A Review," *Tribology International* 44:532-549 (2011), which is hereby incorporated by reference in its entirety). The observed flatness of the curves indicates that large ellipticity deviations from the optimal value can be tolerated without significant degradation in bearing performance. In all cases, the optimal ellipticity is greater than the nominal clearance, further supporting a line contact approach design strategy for spherical bearings under (essentially) pure-squeeze loading conditions.

Figure 20:
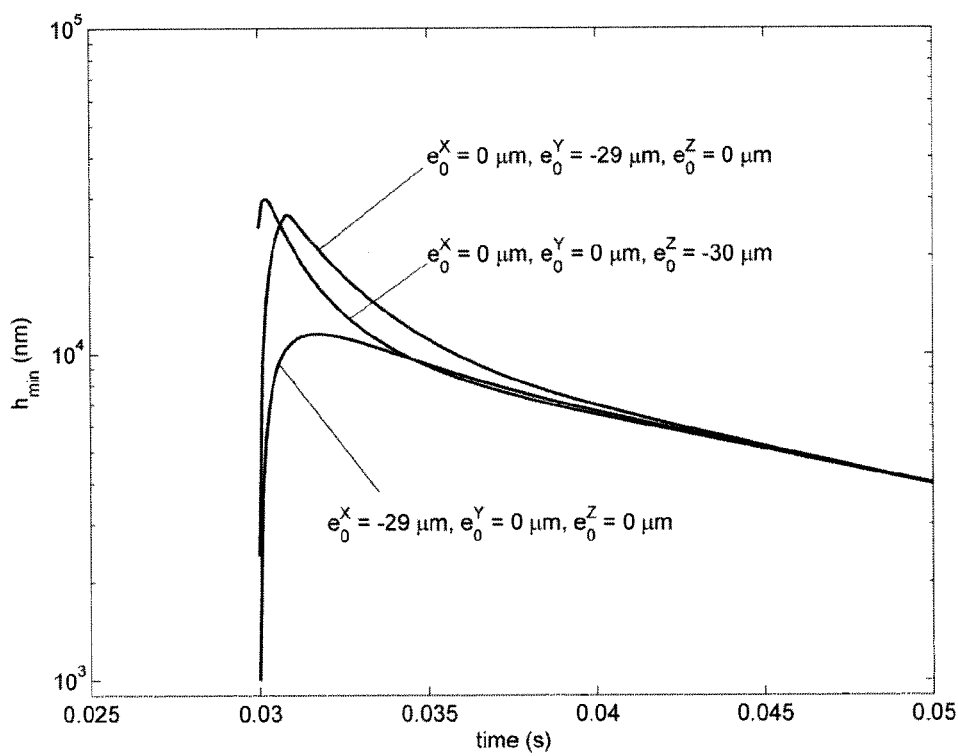
FIG. 20 is a graph showing the effect of initial conditions. $R_1$=16 mm, $\mu$=2.5 mPa·s, $C_0$=30 µm, $\delta$=40 µm.

The swing phase of the gait cycle results in relative separation of ball and cup surfaces, and the position of the ball at the start of the stance phase of the subsequent gait cycle is unknown. Fortuitously, ball-cup relative motion during the swing phase need not be known in detail, since films are thick and pressures low. Even its role in initiating stance-phase motion is fairly arbitrary, since the latter motion is relatively insensitive to plausible initial conditions. FIG. 20 illustrates this insensitivity for time histories of minimum film thickness; corresponding time histories of maximum film pressure curves yield very similar results. It is thus convenient to suppose arbitrarily that stance-phase motion begins from a centered condition at the origin.

Figure 21:
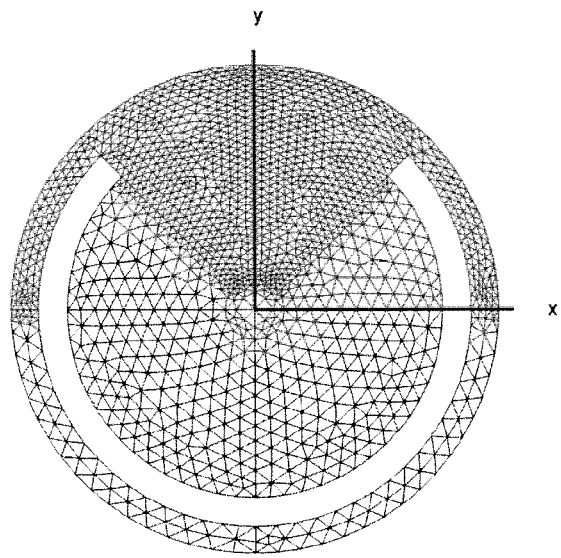
FIG. 21 is a plan view of a film mesh underlying a cup that lacks a cut-away portion, such as that shown in FIG. 6A.
Figure 22A:
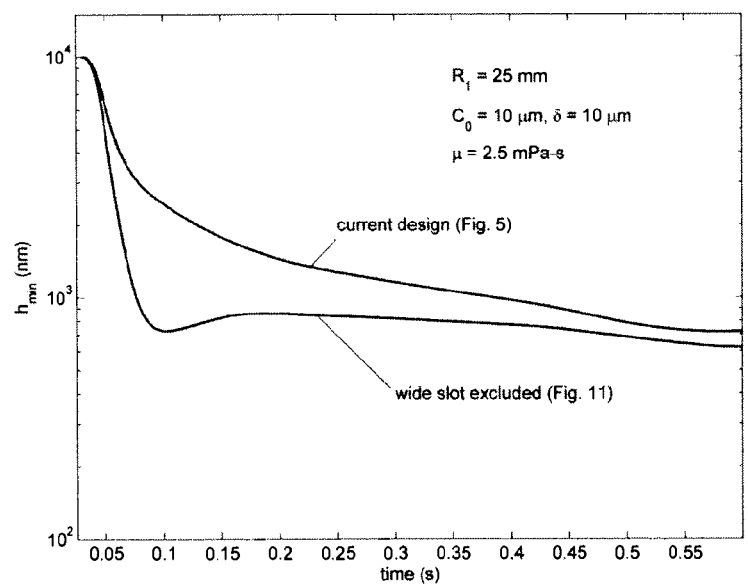
FIGS. 22A-B are graphs showing the effect of wide slot on bearing performance when compared with a complete cup.
Figure 22B:
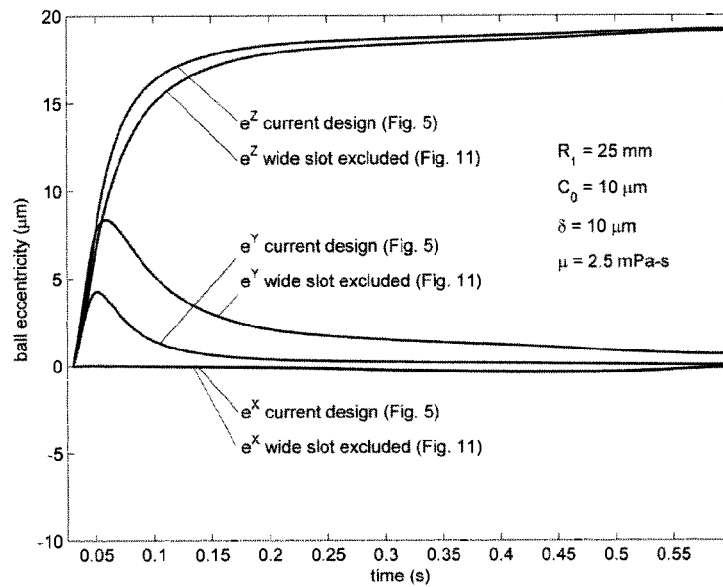

An important design consideration is the wide radial slot on the rigid portion of the cup. FIG. 21 shows the projected view of an essentially complete cup where only the narrow slots remain for the placement of the elastic elements. FIGS. 22A-B show a significant decrease in minimum film thickness with the complete cup at relatively smaller clearance specifications. Peak film pressures are slightly lower with the complete cup due to the availability of additional bearing material. Comparison of corresponding time histories of journal eccentricity reveal that the ball is pushed in the direction of the flexion-extension axis Y as a result of film pressures generated on this additional cup material. The result is normal approach near the edge of the cup instead of along the load line. This detrimental effect of side pressure is less pronounced at larger clearances, but it is desirable to retain the wide slot as a better means of providing lubricant to the load-carrying portion of the film.

Figure 23A:
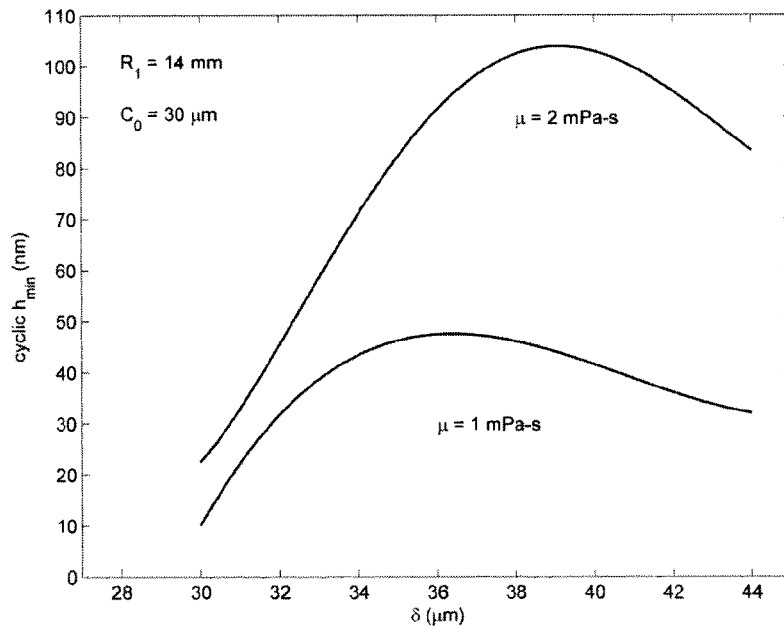
FIGS. 23A-B are graphs showing the effect of ellipticity on bearing performance in one embodiment of an artificial hip joint replacement system of the present invention. In each of these figures, $R_1$=14 µm, $C_0$=30 µm, and the viscosity $\mu$ takes on values of 1 and 2 mPa·s.
Figure 23B:
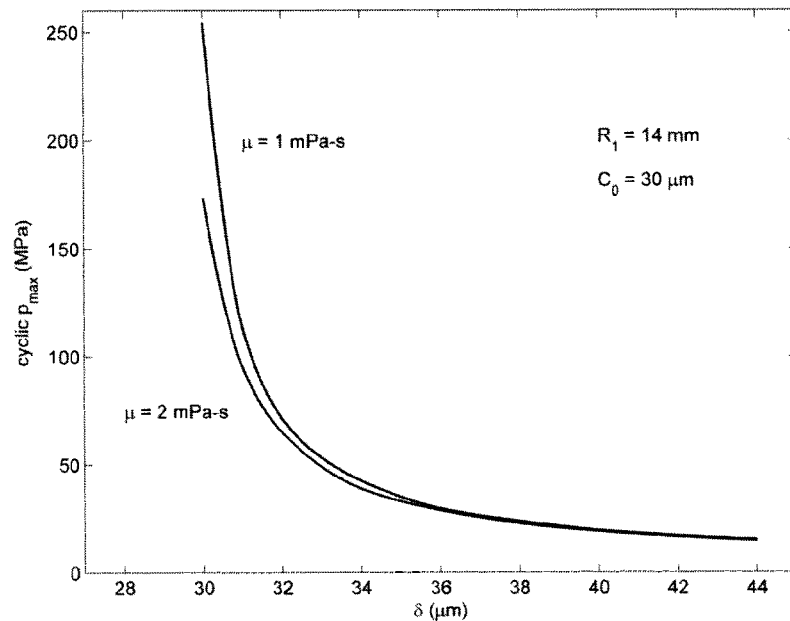

FIGS. 23A-B show the effect of ellipticity magnitude on stance phase extrema values of minimum thickness and cyclic maximum film pressures obtained for ball radii $R_1$=14 mm, nominal clearance $C_0$=30 μm, and viscosity values of 1 and 2 mPa·s. These specifications are employed in the transient EHD studies by Wang et al., "Effect of Non-Spherical Bearing Geometry on Transient Elastohydrodynamic Lubrication in Metal-on-Metal Hip Joint Implants," *Proc. IMechE, Part J: Journal of Engineering Tribology* 221:379-389 (2007) and Meng et al., "Transient Elastohydrodynamic Lubrication Analysis of a Novel Metal-on-Metal Hip Prosthesis with a Non-Spherical Femoral Bearing Surface," *Proc. IMechE, Part H: Journal of Engineering in Medicine* 225:25-37 (2011), which are hereby incorporated by reference in their entirety, where cup and ball ellipticity variations were investigated when subjected to the ISO-standard bearing duty cycle of FIG. 7. Wang et al., "Effect of Non-Spherical Bearing Geometry on Transient Elastohydrodynamic Lubrication in Metal-on-Metal Hip Joint Implants," *Proc. IMechE, Part J: Journal of Engineering Tribology* 221:379-389 (2007), which is hereby incorporated by reference in its entirety, predict cyclic minimum film thickness and maximum film pressure on the order of 20 nm and 50 MPa, respectively, for cup ellipticity specifications up to 6 μm with the 1 mPa·s viscosity specification. The optimal minimum film thickness and maximum film pressure values using the proposed squeeze-film artificial hip joint are observed to be substantially larger and smaller, respectively, than the results in Wang et al., "Effect of Non-Spherical Bearing Geometry on Transient Elastohydrodynamic Lubrication in Metal-on-Metal Hip Joint Implants," *Proc. IMechE, Part J: Journal of Engineering Tribology* 221:379-389 (2007), which is hereby incorporated by reference in its entirety. Moreover, the proposed squeeze-film artificial hip joint produces optimal results with ellipticity specifications which are substantially larger than those employed by Wang et al., "Effect of Non-Spherical Bearing Geometry on Transient Elastohydrodynamic Lubrication in Metal-on-Metal Hip Joint Implants," *Proc. IMechE, Part J: Journal of Engineering Tribology* 221:379-389 (2007), which is hereby incorporated by reference in its entirety.

Meng et al., "Transient Elastohydrodynamic Lubrication Analysis of a Novel Metal-on-Metal Hip Prosthesis with a Non-Spherical Femoral Bearing Surface," *Proc. IMechE, Part H: Journal of Engineering in Medicine* 225:25-37 (2011), which is hereby incorporated by reference in its entirety, predict best-case minimum film thickness and maximum film pressures of 50 nm and 20 MPa, respectively, for a metal-on-metal prosthesis employing a non-spherical "Alpharabola" head and cup geometry with the 2 mPa·s viscosity specification. The optimal minimum film thickness value using the proposed squeeze-film artificial hip joint is observed to be substantially larger than the results in Meng et al., "Transient Elastohydrodynamic Lubrication Analysis of a Novel Metal-on-Metal Hip Prosthesis with a Non-Spherical Femoral Bearing Surface," *Proc. IMechE, Part H: Journal of Engineering in Medicine* 225:25-37 (2011), which is hereby incorporated by reference in its entirety, while peak film pressures are observed to be similar. However, the minimum radial clearance specifications in the Alpharabola design with undeformed ball and cup surfaces are less than 1 µm, while the proposed squeeze-film artificial hip joint produces optimal results with clearance specifications which are substantially larger.

Figure 18A:
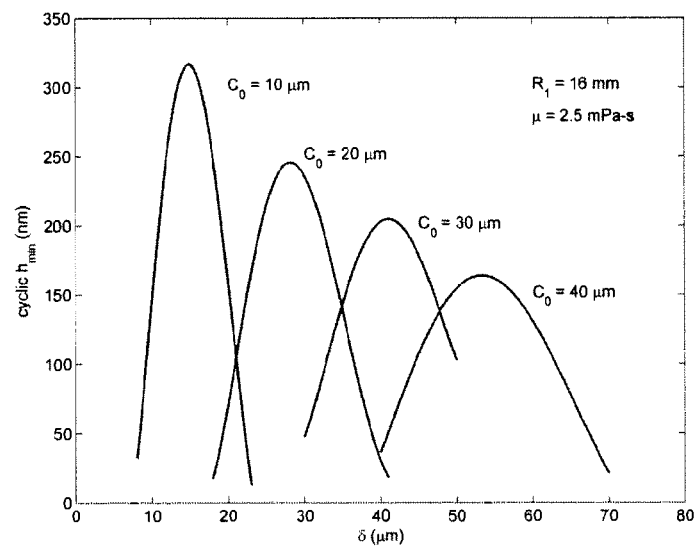
FIGS. 18A-B are graphs showing the effect of ellipticity on bearing performance in one embodiment of an artificial hip joint replacement system of the present invention. In each of these figures, $R_1$=16 µm and $\mu$=2.5 mPa·s.
Figure 18B:
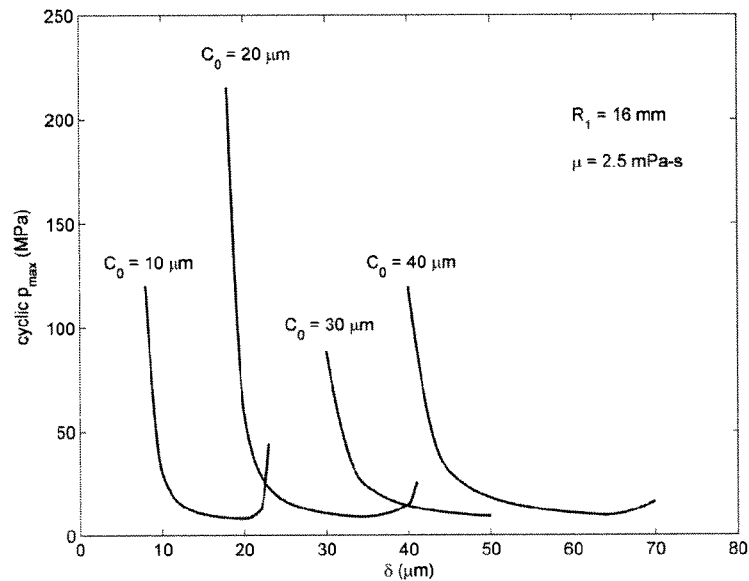
Figure 19A:
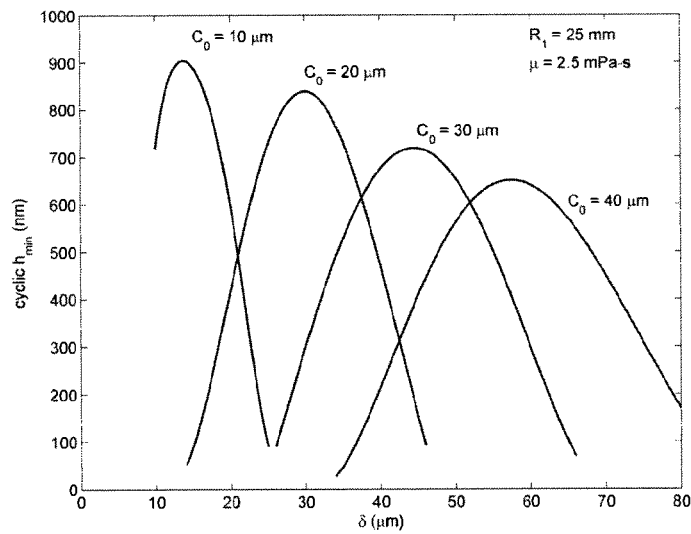
FIGS. 19A-B are graphs showing the effect of ellipticity on bearing performance in one embodiment of an artificial hip joint replacement system of the present invention. In each of these figures, $R_1$=25 µm and $\rho$=2.5 mPa·s.
Figure 19B:
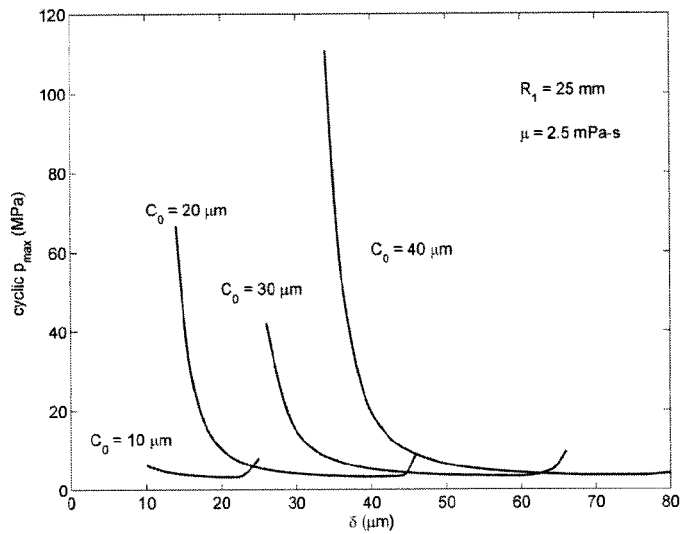
Figure 24A:
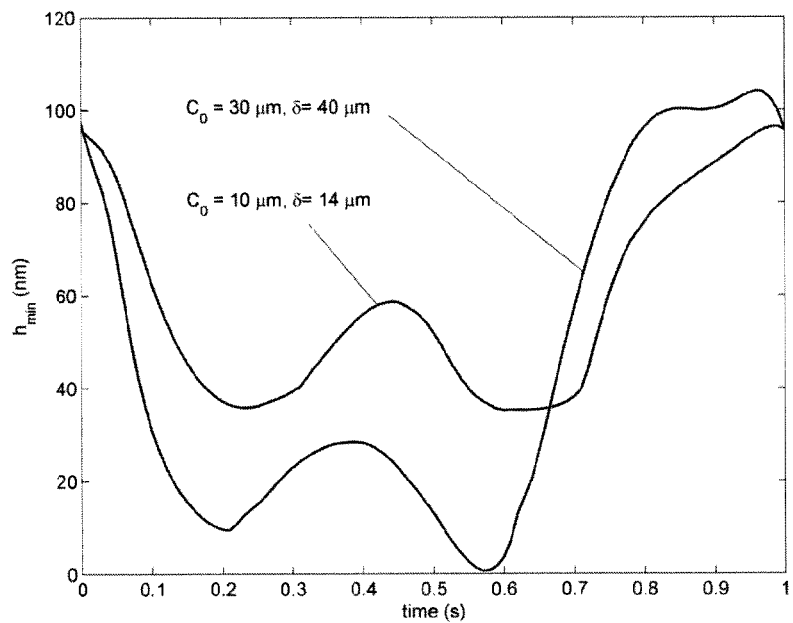
FIGS. 24A-B are graphs showing the effect of ellipticity on periodic time histories of minimum film thickness and maximum film pressure for a complete hemispherical cup.
Figure 24B:
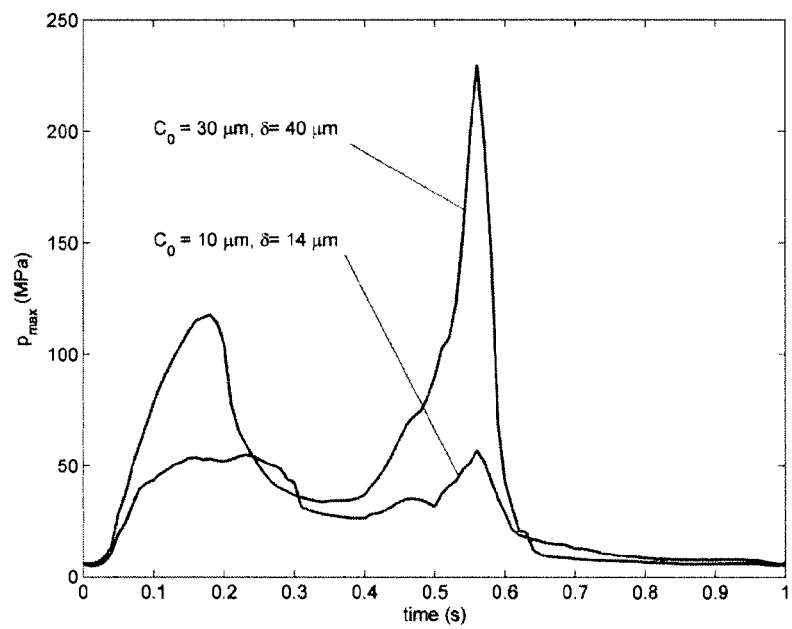

FIGS. 24A-B show periodic time histories of bearing performance for a complete hemispherical cup subjected to the complete periodic duty cycle provided in FIG. 7. In these cases, the elastic elements are absent, and the external load over the entire gait cycle is carried by the lubricant film primarily through wedge-film action. Each simulation is run until solution periodicity is attained. Nominal clearance and ellipticity specifications for ball radius $R_1=16$ mm are chosen based on optimal performance values provided in FIGS. 18A-B. With the relatively tight clearance specification of $C_0=10$ µm and $\delta=14$ µm, the resulting cyclic minimum film thickness and cyclic maximum film pressure values are similar to those obtained by the designs in Wang et al., "Effect of Non-Spherical Bearing Geometry on Transient Elastohydrodynamic Lubrication in Metal-on-Metal Hip Joint Implants," *Proc. IMechE, Part J: Journal of Engineering Tribology* 221:379-389 (2007) and Meng et al., "Transient Elastohydrodynamic Lubrication Analysis of a Novel Metal-on-Metal Hip Prosthesis with a Non-Spherical Femoral Bearing Surface," *Proc. IMechE, Part H: Journal of Engineering in Medicine* 225:25-37 (2011), which are hereby incorporated by reference in their entirety, but the results are substantially smaller and larger, respectively, than the proposed artificial hip joint. The larger clearance specification of $C_0=30$ µm and $\delta=40$ µm yields predicted film thickness values which do not support a hydrodynamic film. Cup ellipticity alone is thus insufficient to enhance lubrication performance.

Closure

This example presents a novel design approach for artificial hip joints by exploiting squeeze-film action to yield substantially thicker lubricant films and smaller lubricant film pressures compared with conventional designs. Optimal squeeze-film bearing performance during the stance-phase portion of the gait cycle is accomplished though ellipsoidal cup geometry with ellipticity specifications which result in circular line contact in the limit of ball-cup relative motion along the load line. The use of elastic columns has been shown to provide a plausible means of separating ball and cup during the low-load stance phase of the gait cycle. Optimal cup clearance specifications in the new design are much larger than those employed in conventional designs.

Of potential concern are the elastic elements which are in constant contact with the ball over the entire gait cycle. However, the portion of the stance phase gait cycle loads carried by the elastic elements is substantially smaller than that carried by the lubricant film, so wear is likely of substantially lesser importance here.

A conservative analysis approach was taken here by assuming ball and cup surface rigidity in the lubrication film regions. As for conventional designs, inclusion of structural elasticity will likely provide even more favorable estimates of bearing performance for the new design. Even so, low squeeze-film pressures produced in the optimal cup designs should not result in significant elastic deformation of the cup regardless of material choice. Thus, a UHMWPE cup with either a metal or ceramic ball is a plausible material combination for the proposed design. The dominant compliance of the proposed design remains the elastic columns.

Example 2

Planar Finite Elements

Formulation

Figure 25:
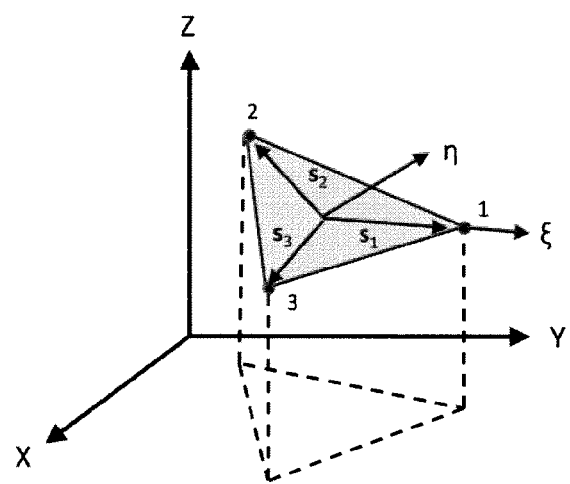
FIG. 25 is an illustration of a planar fluid film element.

FIG. 25 shows a planar triangular fluid film element arbitrarily oriented relative to a system X, Y, Z reference frame. The position vector of the element nodes are denoted as $S_i$, i=1, 3, where $|S_i|=R_2=R$. Define nodal position vectors relative to the element centroid by $$s_i = S_i - (S_1 + S_2 + S_3)/3 \quad (A1)$$

from which a set of orthonormal vectors u, v, n can be formed from $$u = s_1/|s_1| \quad (A2)$$

$$n = s_1 \times s_2/|s_1 \times s_2| \quad (A3)$$

$$v = n \times u \quad (A4)$$

Vector n is normal to the element plane. Vectors u and v lie in the element plane and are employed as unit vectors for a ξ, η film reference frame with its origin at the element centroid. Nodal coordinates relative to the film reference frame are thus given by $$P_i^\xi = s_i \cdot u \quad (A5)$$

$$P_i^\eta = s_i \cdot v \quad (A6)$$

Nodal film thickness and its time rate of change are given by $$h_i = C - e \cdot S_i/R \quad (A7)$$

$$dh_i/dt = -de/dt \cdot S_i/R \quad (A8)$$

For elements which are small compared with the cup radius, $n \approx S_i/R$, with the result that nodal ball surface velocity components in the film reference frame can be expressed by $$V_i^\xi = (\omega \times S_i) \cdot u \quad (A9)$$

$$V_i^\eta = (\omega \times S_i) \cdot v \quad (A10)$$

Formation of fluidity matrices in the film reference frame follows directly from Booker and Huebner, "Application of Finite Element Methods to Lubrication: An Engineering Approach," *ASME Journal of Lubrication Technology* 94:313-323 (1972), which is hereby incorporated by reference in its entirety, or Booker and Boedo, "Finite Element Analysis of Elastic Engine Bearing Lubrication: Theory," Revue Européenne des Éléments Finis 10:705-724 (2001), which is hereby incorporated by reference in its entirety.

Validation

Figure 26A:
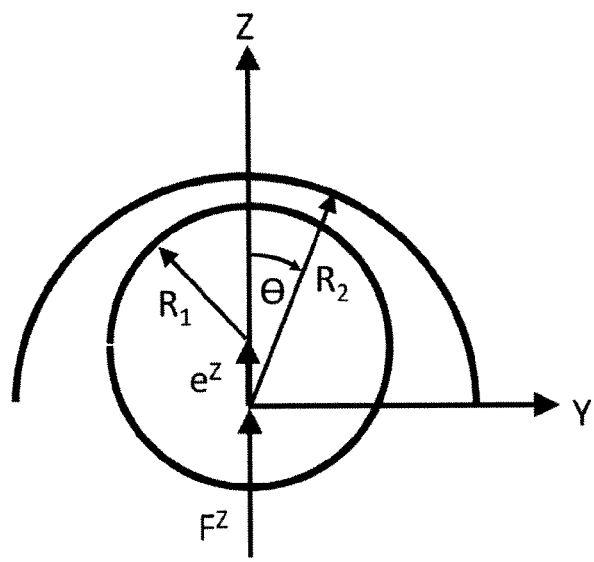
FIGS. 26A-B are illustrations showing a hemispherical bearing under axisymmetric pure squeeze. The X, Y, Z reference frame is attached to the center of the cup with the Z axis passing through the pole of the cup. Angles $\theta$ and $\phi$ and radius $R_2$ are spherical coordinates which locate a point on the hemisphere. The load $F^z$ is directed along the polar axis of symmetry.
Figure 26B:
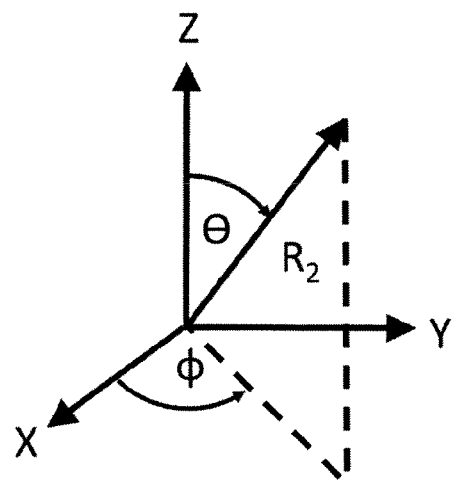

FIGS. 26A-B show a hydrodynamic bearing with a perfectly spherical ball radius $R_1$ and a perfectly hemispherical cup with radius $R=R_2$ under axisymmetric transient squeeze ($e^X = e^Y = 0$). Defining radial clearance $C_0 = R_2 - R_1$ and ball eccentricity ratio $\epsilon = e^Z/C_0$, the pressure distribution p(θ) which satisfies the Reynolds equation and zero (ambient) pressure along the boundary can be obtained in closed form, which when integrated yields (ball to sleeve) load components (Goenka and Booker "Spherical Bearings: Static and Dynamic Analysis via the Finite Element Method," *ASME Journal of Lubrication Technology* 102:308-318 (1980), which is hereby incorporated by reference in its entirety)

$$F^X = F^Y = 0 \quad \text{(A11)}$$

$$F^Z = K\left(\frac{d\varepsilon}{dt}\right)f(\varepsilon) \quad \text{(A12)}$$

where $$K = \pi R^2 \mu / (C_0/R)^2 \quad \text{(A13)}$$

$$f(\varepsilon) = 6\{\ln(1-\varepsilon)/\varepsilon^3 + 1/[\varepsilon^2(1-\varepsilon)] - 1/(2\varepsilon)\}, \quad \varepsilon < 1 \quad \text{(A14a)}$$

$$= 4, \quad \varepsilon = 0 \quad \text{(A14b)}$$

Note that the value of $F^Z$ for $\epsilon=0$ is incorrectly reported in Goenka and Booker "Spherical Bearings: Static and Dynamic Analysis via the Finite Element Method," *ASME Journal of Lubrication Technology* 102:308-318 (1980), which is hereby incorporated by reference in its entirety.

Given initial and final ball eccentricity ratios $\epsilon_0<1$ and $\epsilon_0<E_T<1$ at times t=0 and t=T>0, respectively, the load impulse $$I=\int_0^T F^Z dt \quad \text{(A15)}$$

required to accomplish this task is given by $$I = K\, g(\varepsilon_0, \varepsilon_r) \quad \text{(A16)}$$

where $$g(\varepsilon_0, \varepsilon_T) = 3\{\ln(1-\varepsilon_0)/(\varepsilon_0)^2) - \ln(1-\varepsilon_T)/(\varepsilon_T^2) +$$
$$\ln[(1-\varepsilon_0)/(1-\varepsilon_T)] +$$
$$1/\varepsilon_0 - 1/\varepsilon_T\}, \quad \varepsilon_0 \neq 0, \varepsilon_T \neq 0 \quad \text{(A17a)}$$

$$= -3[\ln(1-\varepsilon_T) + \ln(1-\varepsilon_T)/(\varepsilon_T)^2 +$$
$$1/\varepsilon_T + 1/2], \quad \varepsilon_0 = 0, 0 < \varepsilon_T < 1 \quad \text{(A17b)}$$

$$= 3[\ln(1-\varepsilon_0) + \ln(1-\varepsilon_0)/(\varepsilon_0^2) +$$
$$1/\varepsilon_0 + 1/2], \quad \varepsilon_0 < 0, \varepsilon_T = 0 \quad \text{(A17c)}$$

Given load impulse and initial eccentricity ratio, the final eccentricity ratio can be found using standard root finding methods (such as bisection).

Table 1 shows that the finite element solution of final eccentricity ratio approaches the exact solution for progressively finer meshes over the stated range of specified dimensionless impulse values. Meshes A-D are comprised of 900, 2400, 5400, and 9600 planar equilateral triangular elements, respectively, uniformly distributed over the hemispherical surface. Each numerical simulation is started with concentric ball and cup ($\epsilon_0=0$). It is reassuring to observe that the finite element solution yields conservative estimates of bearing performance in that it overestimates final eccentricity value for a given load impulse.

TABLE 1

Comparison of Final Eccentricity Ratio (with $\epsilon_0 = 0$)

| $\dfrac{I\,(C_0/R)^2}{\pi R^2 \mu}$ | $\varepsilon_T$ | | | | |
|---|---|---|---|---|---|
| | Exact | Mesh A | Mesh B | Mesh C | Mesh D |
| 1 | 0.2182 | 0.2220 | 0.2191 | 0.2186 | 0.2184 |
| 2 | 0.3842 | 0.3903 | 0.3857 | 0.3849 | 0.3846 |
| 5 | 0.6869 | 0.6956 | 0.6891 | 0.6879 | 0.6875 |
| 10 | 0.8876 | 0.8970 | 0.8899 | 0.8886 | 0.8882 |
| 15 | 0.9561 | 0.9659 | 0.9585 | 0.9572 | 0.9567 |
| 20 | 0.9820 | 0.9916 | 0.9845 | 0.9831 | 0.9826 |
| 30 | 0.9968 | —* | 0.9992 | 0.9979 | 0.9974 |

*Negative film thickness encountered during simulation

Note that the dimensionless impulse computed using the ISO load history, viscosity, and bearing dimensions in this paper ranges between 40 and 100,000. The expected final eccentricity values are thus even greater than those given in Table 1, which strongly discourages the use of a spherical ball and spherical cup for the proposed artificial hip joint.

The maximum film pressure ratio depends only on $\epsilon$ and is given by $$p_{max}\pi R^2/F^Z = 3[1/(1-\varepsilon)^2 - 1]/[\varepsilon f(\varepsilon)], \quad \varepsilon < 1 \quad \text{(A18a)}$$

$$= 3/2, \quad \varepsilon = 0 \quad \text{(A18b)}$$

Figure 27:
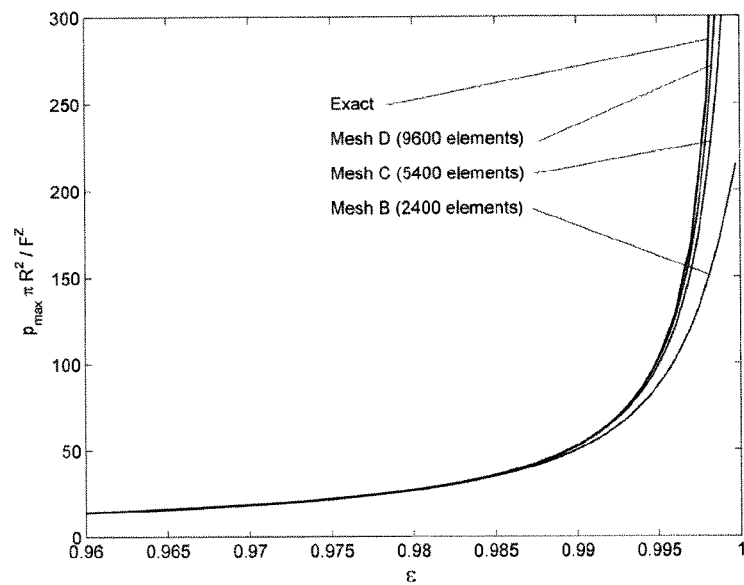
FIG. 27 is a graph showing the results of a mesh refinement study: hemispherical bearing under pure squeeze.

FIG. 27 shows that the finite element solution for maximum film pressure ratio using progressively finer meshes approaches the exact solution for eccentricity ratios over the range $0 \le \epsilon \le 0.998$.

Example 3

Proportional Area Projection

Consider a differential surface area element $(dA)_s = R^2 \sin\theta\, d\theta\, d\phi$ defined on the hemisphere shown in FIG. A2-A-B with $R \equiv R_2$. The spherical differential area is mapped onto a plane with projected differential area $$(dA)_p = r\, dr\, d\phi \quad \text{(B1)}$$

Arbitrarily setting area ratio $J \equiv (dA)_p / (dA)_s$ gives $$JR^2 \int_0^\theta \sin\theta\, d\theta = \int_0^r r\, dr \quad \text{(B2)}$$

so that $$r/R = (2J)^{1/2}(1-\cos\theta)^{1/2} \quad \text{(B3)}$$

A point with spatial coordinates X, Y, Z located on a hemispherical surface of radius R will be mapped to coordinates x, y on the plane using the relations $$x = r\cos\phi \quad \text{(B4)}$$

$$y = r\sin\phi \quad \text{(B5)}$$

where $$\cos\phi = X/(R\sin\theta) \quad \text{(B6)}$$

$$\sin\phi = Y/(R\sin\theta) \quad \text{(B7)}$$

with $$\cos\theta = Z/R \quad \text{(B8)}$$

$$\sin\theta = (1-\cos^2\theta)^{1/2} \quad \text{(B9)}$$

Simplifying gives $$x = X[2J/(1+Z/R)]^{1/2} \quad \text{(B10)}$$

$$y = Y[2J/(1+Z/R)]^{1/2} \quad \text{(B11)}$$

Conversely, a point with coordinates x, y on the plane will be mapped to spatial coordinates X, Y, Z on a hemispherical surface of radius R using the relations $$X = R\sin\theta\cos\phi \quad \text{(B12)}$$

$$Y = R\sin\theta\sin\phi \quad \text{(B13)}$$

$$Z = R\cos\theta \quad \text{(B14)}$$

where $$\cos\theta = 1 - (r/R)^2/(2J) \quad \text{(B15)}$$

$$\sin\theta = (1-\cos^2\theta)^{1/2} \quad \text{(B16)}$$

$$\cos \phi = x/r \quad \text{(B17)}$$

$$\sin \phi = y/r \quad \text{(B18)}$$

with $$r = (x^2 + y^2)^{1/2} \quad \text{(B19)}$$

Simplifying gives $$X = x[4J - (r/R)^2]^{1/2}/(2J) \quad \text{(B20)}$$

$$Y = y[4J - (r/R)^2]^{1/2}/(2J) \quad \text{(B21)}$$

$$Z = R[1 - (r/R)^2/2J] \quad \text{(B22)}$$

Equal-area projections of mesh geometry, film thickness, and film pressure distributions shown in FIG. 15, FIGS. 17A-C, and FIG. 21 were constructed by mapping from spatial coordinates X', Y', Z' and setting J=1.

Example 4

Elastic Element Design

Figure 28A:
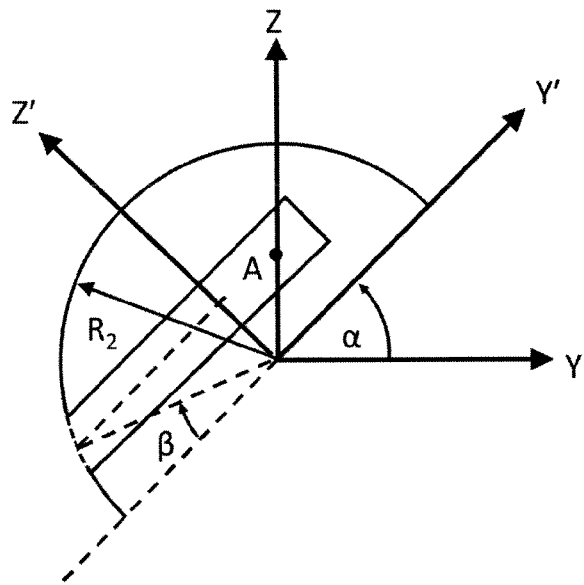
FIGS. 28A-B are illustrations showing the rigid and elastic cup portions in one embodiment of an artificial hip joint replacement system of the present invention.
Figure 28B:
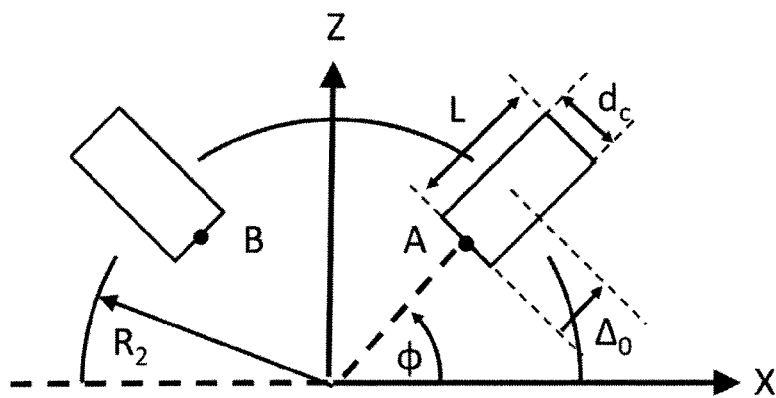

FIGS. 28A-B show sectional views of the elastic and rigid cup portions relative to the system axes defined in FIGS. 6A-B. Each column representing the elastic portion of the cup has a uniform circular cross-section of diameter $d_c$ and unstressed length L. The column axes lie in the X-Z plane and are oriented radially at a common contact angle $\phi$. The columns pass through the narrow slots on the rigid portion of the cup and contact the ball at points A and B. The contact angle $\phi$ is given by $$\sin \phi = \sin \beta / \cos \alpha \quad \text{(C1)}$$

$$\cos \phi = +(1 - \sin^2 \phi)^{1/2} \quad \text{(C2)}$$

which depends upon the cup angle of inclination $\alpha$ and the centerline location of the narrow slots as defined by "latitude" angle $\beta$. In their unstressed state, the columns protrude a radial distance $\Delta_0$ into the ball-cup clearance space, so that at initial contact, the ball is located at a vertical "offset" position $e_0$ along the Z axis defined by $$e_0 \equiv e_0 k = -(\Delta_0 / \sin \phi) k \quad \text{(C3)}$$

For a specified ball eccentricity magnitude $e^z > e_0$, points A and B are equally displaced radially from ball contact, and the resultant elastic load $F_{elast}$ transmitted from ball to cup is given by $$F_{elast} = S(e^z - e_0) k \quad \text{(C4)}$$

in terms of stiffness $$S = (\pi d_c^2 E \sin^2 \phi)/(2L) \quad \text{(C5)}$$

where E is the Young's modulus of the columns, and where linearly elastic deformation of the elastic columns is assumed.

Figure 29:
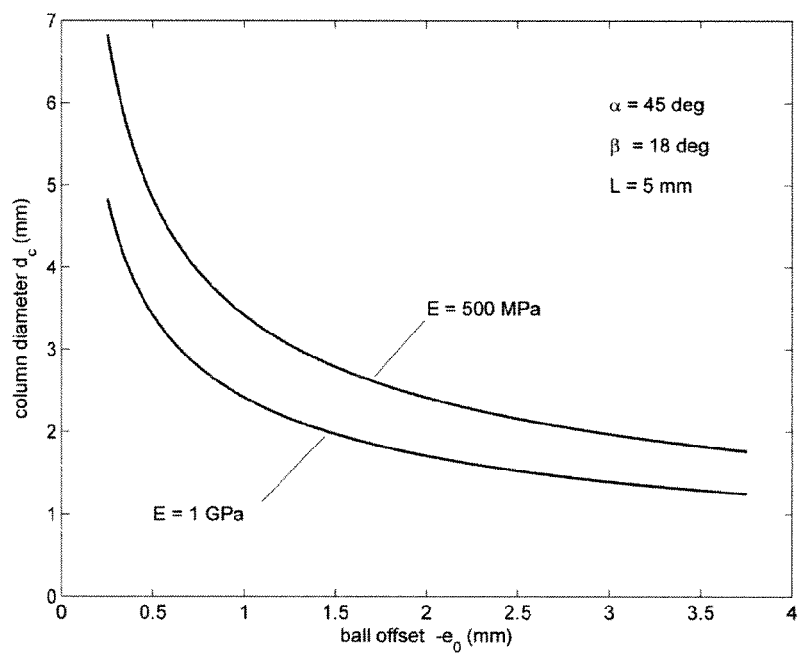
FIG. 29 is a graph showing column diameter required for elastic load of 350N at $e^z$=0.

FIG. 29 shows the required column diameter as a function of ball offset magnitude which results in an elastic load of 350 N when ball and cup are concentric. Biocompatible materials such as UHMWPE fall within the range of Young's modulus values chosen here. Realistic offset specifications are permissible with the rigid cup geometry of FIG. 15 which require that $d_c < 3.18$ mm and $d_c < 4.97$ mm for cup radius specifications $R_2 = 16$ mm and 25 mm, respectively. Since the column stiffness is large and the radial clearance is small, the elastic load increases only a small percentage above the 350 N value for $e^z > 0$.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. An artificial hip joint replacement system comprising:
   an acetabulum portion comprising:
      a cup suitable to be received by a subject's acetabular bone, said cup comprising:
         a rigid portion and
         an elastic portion comprising an elongate finger or tab, a curved beam, or a short rod-like cylinder wherein the elastic portion comprises a proximal end and a distal end, the elastic portion being attached to the rigid portion at some point other than the distal end, wherein the distal end protrudes away from the rigid portion toward an interior region of the cup;
      a ball, having a surface and a center, received by said cup and in contact with the distal end of the elastic portion, wherein the rigid portion has an ellipsoidal shape and the ball has a spherical shape; and
   a femoral stem attached to said ball, wherein the distal end of the elastic portion is positioned to allow a space between said ball and the rigid portion of the cup and cause expansion of the space so the ball and the rigid portion of the cup are further apart from one another during periods of low mechanical loads, and wherein the cup has a center and when the ball and cup centers are coincident, the space between the surface of the ball and the rigid portion of the cup is not uniform.

2. The artificial hip joint replacement system of claim 1 further comprising:
   a shell attached to said cup in a position suitable to be positioned between the subject's acetabular bone and said cup.

3. The artificial hip joint replacement system of claim 1, wherein said elastic portion is an elongate finger or tab having the proximal end attached to said rigid portion.

4. The artificial hip joint replacement system of claim 3, wherein the elongate finger is curved to receive said ball.

5. The artificial hip joint replacement system of claim 3, wherein the rigid portion comprises narrow slots proximate to the elongate finger.

6. The artificial hip joint replacement system of claim 1, wherein the rigid portion and the elastic portion are integrally formed from a single piece of material.

7. The artificial hip joint replacement system of claim 1, wherein the elastic portion is a curved beam.

8. The artificial hip joint replacement system of claim 7, wherein the curved beam has a circular cross-section.

9. The artificial hip joint replacement system of claim 1, wherein the elastic portion is a short rod-like cylinder.

10. The artificial hip joint replacement system of claim 9, wherein the rigid portion comprises a slotted surface.

11. The artificial hip joint replacement system of claim 10, wherein the elastic portion protrudes through the slotted surface of the rigid portion.

12. An artificial hip joint replacement system comprising:
    an acetabulum portion comprising:
       a cup suitable to be received by a subject's acetabular bone, said cup comprising:
          a rigid portion and
          an elastic portion comprising an elongate finger or tab, a curved beam, or a short rod-like cylinder wherein the elastic portion comprises a proximal end and a distal end, the elastic portion being attached to the rigid portion at some point other than the distal end, wherein the distal end protrudes away from the rigid portion toward an interior region of the cup;
a ball, having a surface and center, received by said cup and in contact with the distal end of the elastic portion, wherein the rigid portion has a spherical shape and the ball has an ellipsoidal shape; and
a femoral stem attached to said ball, wherein the distal end of the elastic portion is positioned to allow a space between said ball and the rigid portion of the cup and cause expansion of the space so the ball and the rigid portion of the cup are further apart from one another during periods of low mechanical loads, and wherein the cup has a center and when the ball and cup centers are coincident, the space between the surface of the ball and the rigid portion of the cup is not uniform.

13. The artificial hip joint replacement system of claim 12 further comprising:
a shell attached to said cup in a position suitable to be positioned between the subject's acetabular bone and said cup.

14. The artificial hip joint replacement system of claim 12, wherein said elastic portion is an elongate finger or tab having the proximal end attached to said rigid portion.

15. The artificial hip joint replacement system of claim 14, wherein the elongate finger is curved to receive said ball.

16. The artificial hip joint replacement system of claim 14, wherein the rigid portion comprises narrow slots proximate to the elongate finger.

17. The artificial hip joint replacement system of claim 12, wherein the rigid portion and the elastic portion are integrally formed from a single piece of material.

18. The artificial hip joint replacement system of claim 12, wherein the elastic portion is a curved beam.

19. The artificial hip joint replacement system of claim 18, wherein the curved beam has a circular cross-section.

20. The artificial hip joint replacement system of claim 12, wherein the elastic portion is a short rod-like cylinder.

21. The artificial hip joint replacement system of claim 20, wherein the rigid portion comprises a slotted surface.

22. The artificial hip joint replacement system of claim 21, wherein the elastic portion protrudes through the slotted surface of the rigid portion.

* * * * *